(12) United States Patent
Ilan

(10) Patent No.: US 11,693,000 B2
(45) Date of Patent: Jul. 4, 2023

(54) METHODS AND SYSTEMS FOR MODULATING PHYSIOLOGICAL STATES BETWEEN BIOLOGICAL ENTITIES

(71) Applicant: OBERON SCIENCES ILAN LTD., Kfar Tavor (IL)

(72) Inventor: Yaron Ilan, Kfar Taver (IL)

(73) Assignee: OBERON SCIENCES ILAN LTD., Kfar Tavor (IL)

(*) Notice: Subject to any disclaimer, the term of this patent is extended or adjusted under 35 U.S.C. 154(b) by 741 days.

(21) Appl. No.: 15/776,463

(22) PCT Filed: Nov. 14, 2016

(86) PCT No.: PCT/IL2016/051226
§ 371 (c)(1),
(2) Date: May 16, 2018

(87) PCT Pub. No.: WO2017/085715
PCT Pub. Date: May 26, 2017

(65) Prior Publication Data
US 2018/0328917 A1    Nov. 15, 2018

Related U.S. Application Data

(60) Provisional application No. 62/256,913, filed on Nov. 18, 2015.

(51) Int. Cl.
*A61B 5/00* (2006.01)
*G01N 33/50* (2006.01)
*G16B 45/00* (2019.01)
*A61K 35/26* (2015.01)
*G06F 3/01* (2006.01)
*A61K 31/00* (2006.01)
*A61B 5/24* (2021.01)

(52) U.S. Cl.
CPC .......... *G01N 33/5091* (2013.01); *A61B 5/24* (2021.01); *A61B 5/486* (2013.01); *A61K 31/00* (2013.01); *A61K 35/26* (2013.01); *G06F 3/011* (2013.01); *G16B 45/00* (2019.02); *G01N 2800/52* (2013.01); *G06F 2203/011* (2013.01)

(58) Field of Classification Search
CPC combination set(s) only.
See application file for complete search history.

(56) References Cited

U.S. PATENT DOCUMENTS

| | | | | |
|---|---|---|---|---|
| 8,682,619 | B2* | 3/2014 | Amodei | G01N 33/48 703/1 |
| 8,734,823 | B2* | 5/2014 | Amodei | A61P 43/00 424/422 |
| 2011/0172826 | A1 | 7/2011 | Amodei et al. | |

OTHER PUBLICATIONS

Popien et al. "Eye Gaze tracking reveals heightened attention to food in adults with binge eating when viewing images of real-world scenes" Appetite 91(2015) 233-240 (Year: 2015).*

(Continued)

*Primary Examiner* — Shirley X Jian
(74) *Attorney, Agent, or Firm* — The Roy Gross Law Firm, LLC; Roy Gross

(57) ABSTRACT

The invention provides methods and systems for the treatment and diagnosis of pathologic disorders by modulating a physiological state of a target biological entity via exposure of the target entity to a single or a plurality of triggered entities and for transferring of information in a non-direct way and as part of virtual reality interactive environment.

6 Claims, 6 Drawing Sheets

(56) References Cited

OTHER PUBLICATIONS

Dartmouth Undergraduate Journal of Science "Why Do We Cry?" <https://sites.dartmouth.edu/dujs/2013/02/12/why-do-we-cry/> (Year: 2013).*
Giel et al. "Attentional Processing of Food Pictures in Individuals with Anorexia Nervosa—An Eye-Tracking Study" Biol Psychiatry 2011:69:661-667 (Year: 2011).*
Attridge, et al, Homeostasis and function of regulatory T cells (Tregs) in vivo: lessons from TCR-transgenic Tregs, Immunol Rev 2014, pp. 23-39, vol. 259, No. 1.
Chen, et al., A review of metasurfaces: physics and applications, Rep Prog Phys, Mar. 9, 2016, pp. 1-59.
Wolpaw, et al, Brain-computer interface technology: a review of the first international meeting, IEEE Trans Rehabil Eng, Jun. 2000, pp. 164-173, vol. 8, No. 2.
Grau, et al, Conscious brain-to-brain communication in humans using non-invasive technologies, PLoS ONE, Mar. 2015, vol. 9, No. 8.
Murphy, et al, Current Challenges Facing the Translation of Brain Computer Interfaces from Preclinical Trials to Use in Human Patients, Frontiers in cellular neuroscience, Jan. 6, 2016, vol. 9, No. 497.
Yoo, et al, Non-invasive brain-to-brain interface (BBI): establishing functional links between two brains, PLoS ONE, Apr. 2013, vol. 8, No. 4.
Heinrich, H, Assessment of non-sinusoidal, pulsed, and intermittent exposure to low frequency electric and magnetic field, Health Phys, Jun. 2007, pp. 541-546, vol. 92 No. 6.
Xiao, et al., Wave optics simulation approach for partial sptially coherent beams, Opt Express, Aug. 2006, pp. 6986-6992, vol. 14 No 16.
Wiersma, DS, Random quantum networks, Science, Mar. 12, 2010, pp. 1333-1334, vol. 327, No. 5971.
Feuerer, et al, Foxp3+ regulatory T cells: differentiation, specification, subphenotypes, Nat Immunol, Jul. 2009, pp. 689-695, vol. 10, No. 7.
Ohkura, et al, Regulatory T cells: roles of T cell receptor for their development and function, Semin Immunopathol, Jun. 2010, pp. 95-106, vol. 32, No. 2.
Gor, et al, THi-TH2: a procrustean paradigm, Nat Immunol, Jun. 2003, pp. 503-505, vol. 4 No. 6.
Zhou, S-A, Bioelectrodynamics in living organisms, International Journal of Engineering Science, Jan. 2006, pp. 67-92, vol. 44, No. 1.
http://discovermagazine.com/2007/jun-life-is-rad. everything Emits Radiation—Even You, Discover.
http://www.world-nuclear.org/info/Safety-and-Security/Radiation-and-Health/Radiation-and-Life/, Radiation and Life, Dec. 2012, World Nuclear Association.
Shahbazi-Gahrouei, et al, A review on natural background radiation, Adv Biomed Res, Jul. 30, 2013, vol. 2, No. 65.
Radiation (2015) https://en.wikipedia.org/wiki/Radiation.
Annabi, et al, 25th anniversary article: Rational design and applications of hydrogels in regenerative medicine, Adv Water, Jan. 8, 2014, pp. 85-123, vol. 26, No. 1.
Wichuk, et al, Biotechnological production of value-added carotenoids from microalgae: Emerging technology and prospects, Bioengineered, May-Jun. 2014, pp. 204-208, vol. 5, No. 3.
Kong, et al (2014), Recent advances in understanding the molecular mechanism of chloroplast photorelocaation movement, Biochem Biophys Acta, Apr. 2014, pp. 522-530, vol. 1837, No. 4.
Dellinger, et al (2014), Continuing to illuminate the mechanisms underlying UV-mediated melanomagenesis, J Photochem Photobiol B, Sep. 5, 2014, pp. 317-323, vol. 138.
Lee, Shuk-ming, Oiivia, Radiation emitted by Human Body—Thermal Radiation, Sep. 2010.
Radioactive? AOB, http://hps.org/publicinformation/ate/faqs/faqradbods.html.
Schenck, John F, Physical interactions of static magnetic fields with living tissues, Prog Biophys Mol Biol, Feb.-Apr. 2005, pp. 185-204, vol. 87 No. 2-3.
Baker, et al, Optical control of protein function through unnatural amino acid mutagenesis and other optogenetic approaches, ACS Chem Biol, Jul. 18, 2014, pp. 1398-1407, vol. 9, No. 7.
Holleboom, et al, The back and forth of energy transfer between carotenoids and chlorophylls and its role in the regulation of light harvesting, Photosynth Res, Feb. 2014, pp. 215-221, vol. 119, No. 1-2.
Caballero, et al, Recommendations of the Spanish Societies of Radiation Oncology (SEOR), Nuclear Medicine & Molecular Imaging (SEMNiM), and Medical Physics (SEFM) on (18)F-FDG PET-CT for radiotherapy treatment planning, Cooperative Group for PETCTiRTP, Rep Pract Oncol Radiother, 2012, pp. 298-318, vol. 17.
Campbell, et al., FOXP3 modifies the phenotypic and functional properties of regulatory T cells, Nat Rev Immunol, Apr. 2007, pp. 305-310, vol. 7, No. 4.
Juutilainen, et al, Review of possible modulation-dependent biological effects of radiofrequency fields, Bioelectromagnetics, Oct. 2011, pp. 511-534, vol. 32, No. 7.
Naarala, et al, Cellular Effects of Electromagnetic Fields, Altern Lab Animals, Oct. 2004, pp. 355-360, vol. 32, No. 4.
International Search Report PCT/IL2016/051226 Completed Mar. 9, 2017; dated Mar. 14, 2017 5 pages.
Written Opinion of the International Searching Authority PCT/IL2016/051226 dated Mar. 14, 2017 5 pages.

* cited by examiner

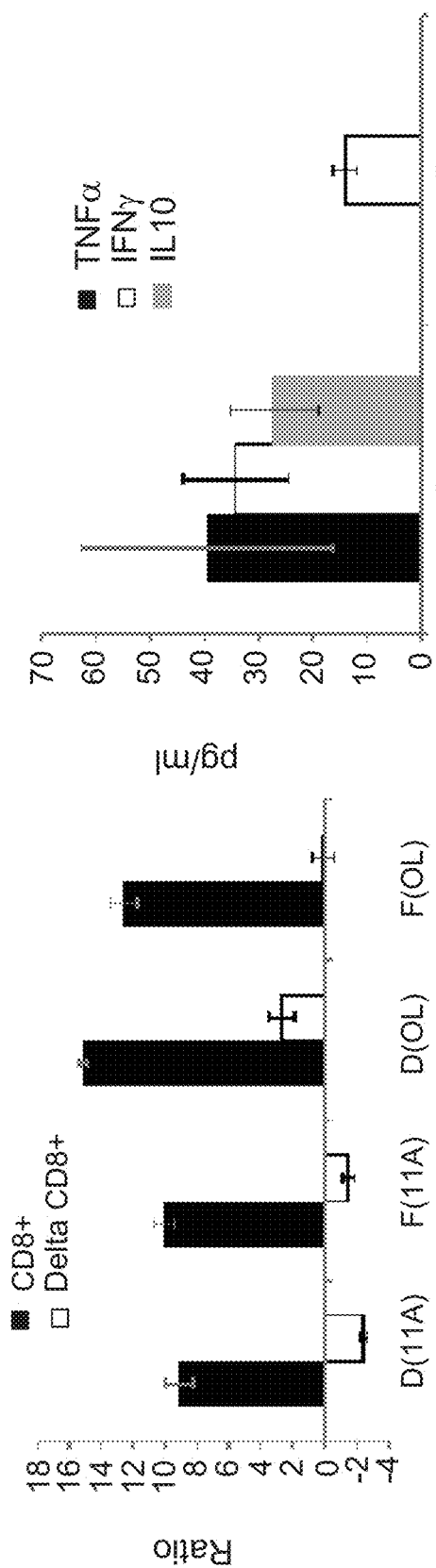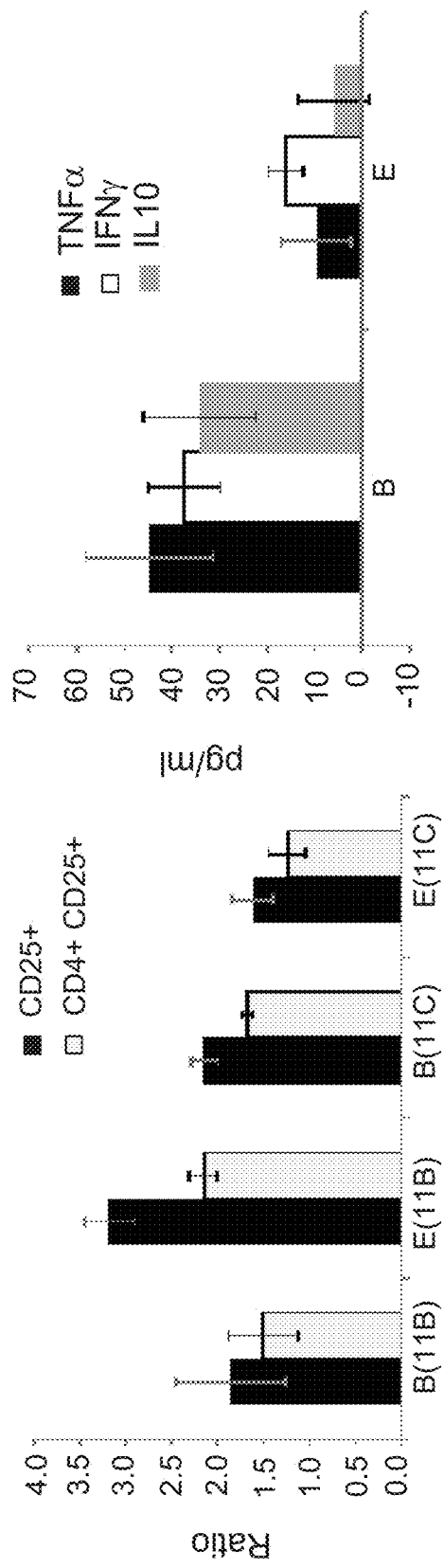
Fig. 2A Fig. 2B Fig. 2C Fig. 2D

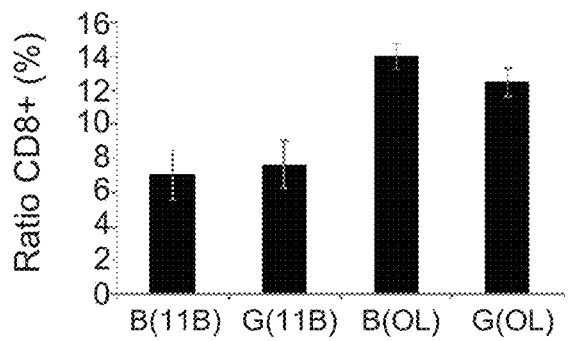
Fig. 3A
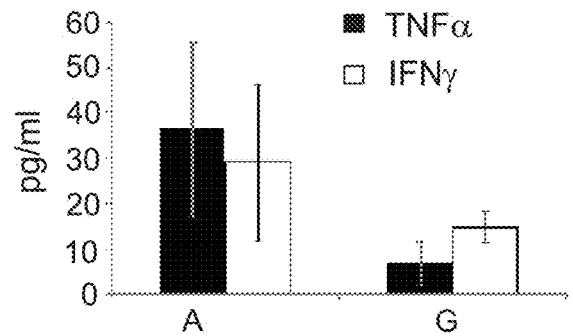
Fig. 3B
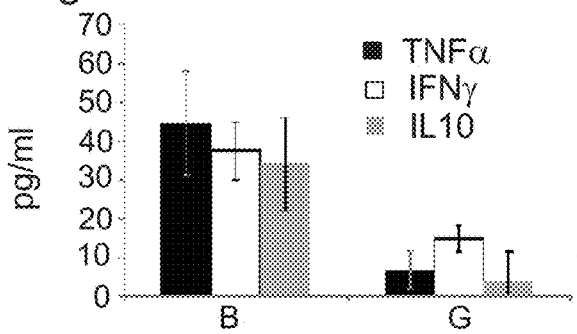
Fig. 3C
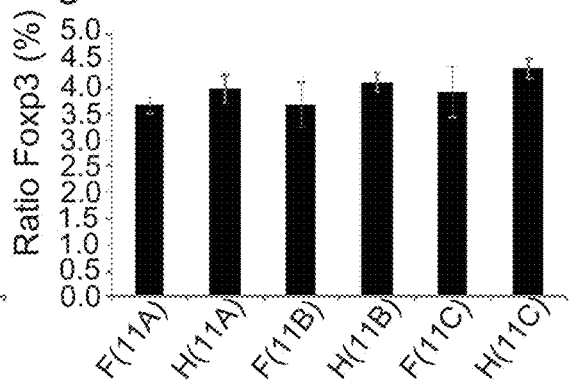
Fig. 3D
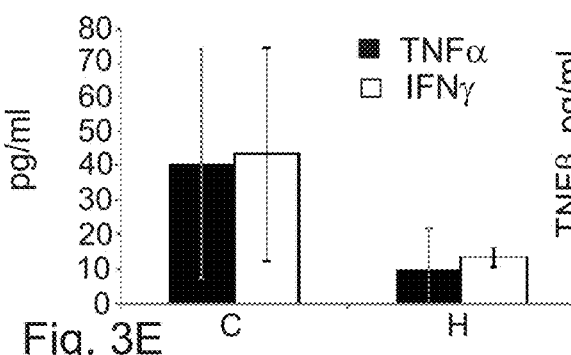
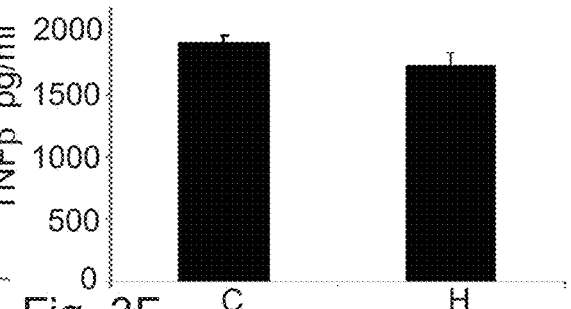
Fig. 3E
Fig. 3F
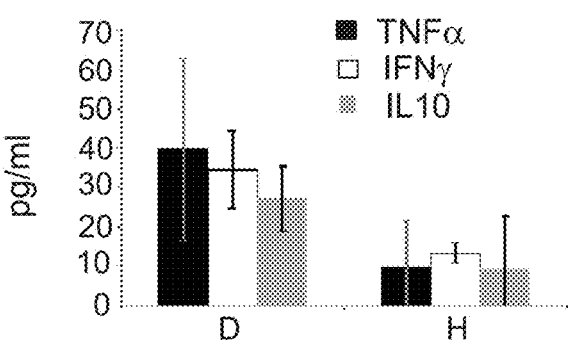
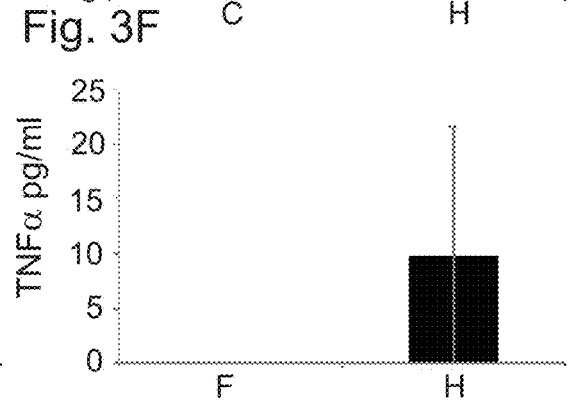
Fig. 3G
Fig. 3H

METHODS AND SYSTEMS FOR MODULATING PHYSIOLOGICAL STATES BETWEEN BIOLOGICAL ENTITIES

RELATED APPLICATIONS

This application is a National Phase of PCT Patent Application No. PCT/IL2016/051226 having International filing date of Nov. 14, 2016, which claims the benefit of priority of U.S. Provisional Application No. 62/256,913 filed on Nov. 18, 2015 entitled METHODS AND SYSTEMS FOR MODULATING PHYSIOLOGICAL STATES BETWEEN BIOLOGICAL ENTITIES. The contents of the above applications are all incorporated by reference as if fully set forth herein in their entirety.

FIELD OF THE INVENTION

The invention relates to non-invasive therapeutic and diagnostic methods and systems. More specifically, the invention provides methods and systems for the treatment and diagnosis of pathologic disorders by modulating physiological states, specifically, an immunological state of a target biological entity via exposure of the target entity to a single or a plurality of triggered entities. The use of the method and systems of the invention in virtual reality devices, products and methods is further provided herein.

BACKGROUND REFERENCES

1. Campbell D J, Ziegler S F: FOXP3 modifies the phenotypic and functional properties of regulatory T cells. *Nat Rev Immunol* 2007, 7(4):305-310.
2. Attridge K, Walker L S: Homeostasis and function of regulatory T cells (Tregs) in vivo: lessons from TCR-transgenic Tregs. *Immunol Rev* 2014, 259(1):23-39.
3. Harris W F: Wavefronts and their propagation in astigmatic optical systems. *Optometry and vision science: official publication of the American Academy of Optometry* 1996, 73(9):606-612.
4. Chen H T, Taylor A J, Yu N: A review of metasurfaces: physics and applications. *Rep Prog Phys* 2016, 79(7): 076401.
5. Wolpaw J R, Birbaumer N, Heetderks W J, McFarland D J, Peckham P H, Schalk G, Donchin E, Quatrano L A, Robinson C J, Vaughan T M: Brain-computer interface technology: a review of the first international meeting. *IEEE Trans Rehabil Eng* 2000, 8(2):164-173.
6. Grau C, Ginhoux R, Riera A, Nguyen T L, Chauvat H, Berg M, Amengual J L, Pascual-Leone A, Ruffini G: Conscious brain-to-brain communication in humans using non-invasive technologies. *PLoS ONE* 2014, 9(8): e105225.
7. Murphy M D, Guggenmos D J, Bundy D T, Nudo R J: Current Challenges Facing the Translation of Brain Computer Interfaces from Preclinical Trials to Use in Human Patients. *Frontiers in cellular neuroscience* 2015, 9:497.
8. Yoo S S, Kim H, Filandrianos E, Taghados S J, Park S: Non-invasive brain-to-brain interface (BBI): establishing functional links between two brains. *PLoS ONE* 2013, 8(4):e60410.
9. Heinrich H: Assessment of non-sinusoidal, pulsed, or intermittent exposure to low frequency electric and magnetic fields. *Health Phys* 2007, 92(6):541-546.
10. Xiao X, Voelz D: Wave optics simulation approach for partial spatially coherent beams. *Opt Express* 2006, 14(16):6986-6992.
11. Naarala J, Hoyto A, Markkanen A: Cellular effects of electromagnetic fields. *Altern Lab Anim* 2004, 32(4):355-360.
12. Juutilainen J, Hoyto A, Kumlin T, Naarala J: Review of possible modulation-dependent biological effects of radiofrequency fields. *Bioelectromagnetics* 2011, 32(7): 511-534.
13. Toohey R E, Keane A T, Rundo J: Measurement techniques for radium and the actinides in man at the Center for Human Radiobiology. *Health Phys* 1983, 44 Suppl 1:323-341.

BACKGROUND OF THE INVENTION

Most living systems contain information. The more complex the system is, the higher the probability that it carries information. For example, the transfer of information between components of the immune system always involves reactions mediated by direct association between different elements of this system. Current paradigms of immune crosstalk between cells (or at subcellular molecular levels) are based on transportation of "classical" immune signals, direct contact between components, or on mediators that transmit information in both health and disease states. These elements serve as links for relocating data. Lymphocyte expression of cell surface markers and cytokines secretion involve messages delivered by molecules (e.g., chemokines) that are secreted by different subsets of cells that transmit a direct signal to a target cell or to a subcellular organelle (e.g., receptor) via physical contact or a messenger molecule [1].

The immune system, similar to other biological pathways, may optimize functionality, but it does not necessarily have perfect structure or symmetry. No evidence for information transfer between components of the immune system, or for an ability to alter a constituent of this system, without directly affecting one of its associate parts has been reported.

Expression of cell surface markers on lymphocytes and cytokine secretion involves different pathways. Transportation of "classical" immune signals is based on messages delivered by molecules (e.g. chemokines) secreted by different subsets of cells which transmit a direct signal to a target cell or to a sub-cellular organelle (e.g. receptor) via a physical contact or a messenger molecule [2].

Electromagnetic radiation (EMR) is a form of radiant energy released by certain electromagnetic processes. EMR consists of electromagnetic waves, which are synchronized oscillations of electric and magnetic fields that propagate [3]. The oscillations of the two fields are perpendicular to each other and perpendicular to the direction of energy and wave propagation, forming a transverse wave. EM waves carry energy, momentum and angular momentum away from their source particle and impart those quantities to matter with which they interact [4].

Radiation, in the sense of an emission or transmission of energy or particles in the form of waves, includes electromagnetic radiation such as radio waves, visible light, and x-rays, particle radiation such as a, (3, and neutron radiation and acoustic radiation such as ultrasound, sound, and seismic waves. For certain types of radiation it is either ionizing or non-ionizing depending on the energy of radiated particles. Ionizing radiation carries more than 10 eV, which is sufficient to ionize atoms and molecules, and break chemical bonds. This distinction is useful for evaluation of potential risks to living organisms. A common source of ionizing radiation is radioactive materials that emit α, β, or γ radiation. Other sources include X-rays from medical radiography examinations, and muons, mesons, positrons, neutrons and other particles that constitute the secondary cosmic rays that are produced after primary cosmic rays interact with Earth's atmosphere. It has been suggested that living species are capable of producing certain types of electromagnetic radiation. Biological and physiological effects of such radiation have not been sufficiently explored [3, 4].

Electromagnetic radiation (EMR) is a form of radiant energy released by certain electromagnetic processes. Classically, EMR consists of electromagnetic waves, which are synchronized oscillations of electric and magnetic fields that propagate. The oscillations of the two fields are perpendicular to each other and perpendicular to the direction of energy and wave propagation, forming a transverse wave. EM waves carry energy, momentum and angular momentum away from their source particle and impart those quantities to matter with which they interact. Human sensory and motor systems provide the natural means for the exchange of information between individuals. Brain-computer interface (BCI) technology was developed as a communication method for those with neuromuscular impairments that prevent them from using conventional augmentative communication methods. BCI's offer communication channels that do not depend on peripheral nerves, and provides an important element for brain-to-brain communication systems. BCI's use electroencephalographic (EEG) activity to control cursor movement, select letters or icons, or operate a neuroprosthesis. The application of brain-machine interfaces (BMIs) to neuroprosthesis provides an approach to treat patients with sensorimotor impairments. BMI systems use motor intent signals to activate paretic muscles or to modulate the spinal cord in a way that reengage dormant neuromuscular systems below the level of injury. The central element in each BCI is a translation algorithm that converts electrophysiological input from the user into output that controls external devices.

BCI depends on interaction between two adaptive controllers, the user who encodes his commands in the electrophysiological input provided to the BCI, and the BCI which recognizes the commands contained in the input and expresses them in device control [5] [6],[7].

Transmission of information between human brains through the intact scalp and without intervention of motor or peripheral sensory systems was described[6]. Pseudo-random binary streams encoding words were transmitted between minds of emitter and receiver subjects separated by great distances, representing a human brain-to-brain interface [6]. A model using a non-natural computer-brain interface to induce an out-of-body effect was reported and showed non-invasive information transfer between the brains of different species [8]. The translation of the intention of a human volunteer to stimulate the rat brain motor area responsible for tail movement was shown. The data suggested the feasibility of a computer-mediated brain-to-brain interface that links neural functions between two biological entities.

There is therefore need to provide therapeutic and diagnostic methods and systems based non-invasive and indirect transfer of information between at least one target biological entity and a single or plurality of entities. There is further need for adapting non-invasive therapeutic and diagnostic methods and systems for use in virtual reality systems.

SUMMARY OF THE INVENTION

The inventive concept behind the above-referred to methods and systems of the present invention stems from the notion that biological entities are capable of producing certain types of waveform transmission, e.g. electromagnetic radiation, radio waves, sound waves, microwaves, infrared radiation, visible light, ultraviolet radiation, X-rays, and gamma rays, and if triggered this radiation may be used to induce changes in another biological or non-biological entity.

In one of its main aspects, the invention provides a method for modulating a physiological state of a target biological entity by exposing said target entity to a single or a plurality of triggered entities in a non-direct way. More specifically, the method comprising (a) providing a single or a plurality of other entities, wherein at least one of said other entities is a biological entity. (b), subjecting at least one of said other entities to a trigger. (c) exposing the target entity to at least one of the triggered entity obtained in (b), thereby modulating a physiological state of the target biological entity.

In another aspect, the present invention relates to a therapeutic method applicable for various physiological conditions, which comprises an exposure of a subject suffering from a pathological condition to a single or a plurality of biological entities and non-biological entities subjected to a stimulus or trigger. In certain embodiments, such exposure is performed in a non-invasive and an in-direct manner.

Another important aspect of the present invention relates to a diagnostic method for detecting pathological conditions, which comprises an exposure of a subject to be diagnosed to a single or a plurality of biological entities and non-biological entities, and further comprises measuring at least one end point indication in said biological entities and non-biological entities.

It is another important aspect of the present invention to provide a system comprising a single or a plurality of biological entities and non-biological entities, which is capable of carrying out the above therapeutic and diagnostic applications.

Still further aspects of the invention provide virtual reality product or device comprising the system of the invention. In yet another aspect, the invention provides virtual reality applications of the therapeutic and diagnostic methods provided herein.

These and other aspects of the invention will become apparent by the hand of the following description.

BRIEF DESCRIPTION OF THE FIGURES

FIG. 1A shows CD8+CD25+ cell count (%) in samples of autogeneic lymphocytes exposed to mice from group A (fasting) vs. group C (non-fasting) in two independent experiments (p=0.02 and p=0.019, experiments 11B and 11C, respectively).

FIG. 1B shows TNFα levels (pg/ml) in samples of syngeneic lymphocytes exposed to mice from group E (fasting) vs. group F (non-fasting) groups (p=0.047).

FIG. 2A to FIG. 2D show the effect of exposure to immunologically compromised mice subjected to splenectomy on the immunological outcomes of samples of syngeneic lymphocytes referring to groups detailed in Table 1.

FIG. 2A shows CD8+ cell count (%) and ΔCD8+(between 0 and 24 h time points) in lymphocyte samples exposed to mice from group D (splenectomized) vs. group F (non-splenectomized) in two independent experiments (ΔCD8+ p=0.021 and p=0.021 for experiments 11A and OL, respectively).

FIG. 2B shows TNFα, IFNγ and IL10 levels (pg/ml) in lymphocyte samples exposed as in FIG. 2A (p=0.014, p=0.021 and p=0.013, respectively, groups D vs. F).

FIG. 2C shows CD25+ and CD4+CD25+ cell counts (%) in lymphocyte samples exposed to mice from groups B (splenectomized) vs. E (non-splenectomized) in two experiments (p=0.02, p=0.021 and p=0.03, p=0.034 for experiments 11B and 11C, respectively).

FIG. 2D shows cytokines TNFα, IFNγ and IL10 levels (pg/ml) in lymphocyte samples exposed as in FIG. 2C (p=0.021, p=0.02 and p=0.02, respectively, groups B vs. E).

FIG. 3A to FIG. 3H show immunological outcomes of lymphocyte samples exposed to mice subjected to splenectomy and fasting (groups A, B) or splenectomy alone (groups C, D) vs. non-exposed lymphocytes (kept on empty cages, groups G or H) in four independent experiments (11A, 11B, 11C and OL) referring to groups detailed in Table 1.

FIG. 3A shows CD8+ cell count (%) in samples of syngeneic lymphocytes exposed to mice from group B vs. samples exposed to empty cages (G) in two experiments (p=0.034 and p=0.043 for experiments 11B and OL, respectively).

FIG. 3B shows TNFα, IFNγ levels (pg/ml) in samples of autogeneic lymphocytes exposed to mice from group A vs. samples exposed to empty cages (G) (p=0.021 and p=0.028, respectively).

FIG. 3C shows TNFα, IFNγ and IL10 levels (pg/ml) in samples of syngeneic lymphocytes exposed as in FIG. 3A, groups B vs. G (p=0.021, p=0.021 and p=0.018, respectively).

FIG. 3D shows Foxp3 T-cell marker levels (%) in samples of syngeneic lymphocytes exposed to mice from group F (non-splenectomized and non-fasting) vs. group H (empty cages) in three experiments (p=0.083, p=0.081 and p=0.083, for 11A, 11B and 11C respectively).

FIG. 3E shows TNFα and IFNγ levels (pg/ml) in samples of autogeneic lymphocytes exposed to mice from group C (splenectomy alone) vs. group H (empty cages) (p=0.020).

FIG. 3F shows TNFα levels (pg/ml) in samples exposed as in FIG. 3E, groups C vs. H (p=0.43).

FIG. 3G shows TNFα, IFNγ and IL10 levels (pg/ml) in samples of syngeneic lymphocytes exposed to group D (splenectomy) vs. group H (empty cages) (p=0.021).

FIG. 3H shows TNFα levels in samples of syngeneic lymphocytes exposed as in FIG. 3D, groups F vs. H (p=0.047)

FIG. 5A shows serum ALT, AST levels (IU) in Con A mice exposed to Con A mice treated with Dexamethasone vs. non-treated Con A mice (p<0.01).

FIG. 5B shows IFNγ levels (pg/ml) in the same groups as in FIG. 5A (p<0.01).

DETAILED DESCRIPTION OF THE INVENTION

Figure 1A:
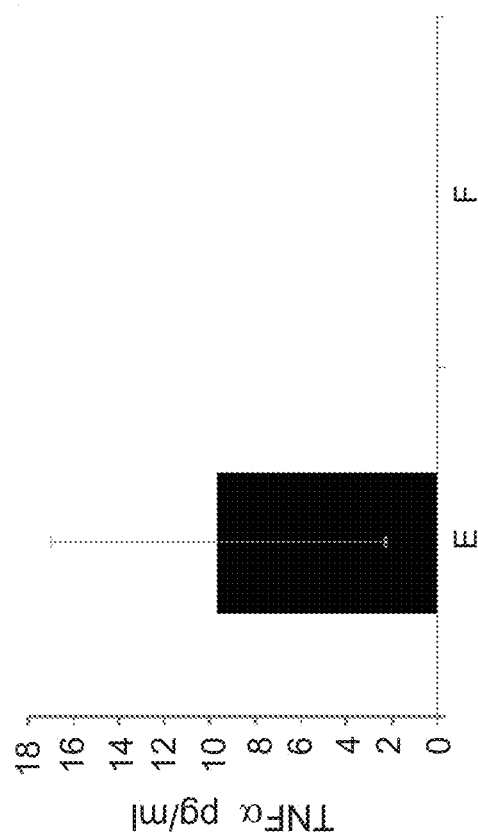
FIG. 1A to FIG. 1B show the effect of exposure to immunologically compromised mice subjected to fasting on the immunological outcomes of samples of autogeneic or syngeneic lymphocytes referring to groups detailed in Table 1.

Transfer of information between components of the immune system is thought to require mediators that directly associate between elements of the immune system. Non-direct transfer of information was not previously described between out of body components of the immune system and the immune system of a subject. Specifically, no evidence for an ability to alter a constituent of the immune system without a direct effect on one of its components was shown.

The present invention describes methods and systems providing non-direct information transfer between entities in an isolated biological model. The described methods and systems may be based, in some embodiments thereof and without wishing to be bound by theory, on electromagnetic wave(s) as a mean of transferring information. Thus, electromagnetic waves may serve as a useful tool for immune information processing without the transfer of "classical" signals.

The noted effects cannot be explained by classical immunology and are therefore may suggest in some embodiments thereof, of a wave-dependent manner of information transfer in the described system. The system described herein provides a robust model for biological applications of information transfer in immunological and in biological systems. The model demonstrated herein may be also used as an elementary constituent of a wave repeater in other biological systems. The state implemented in this protocol is based on complex systems for altering the surface markers and cytokine secretion of lymphocytes. The present invention demonstrates the feasibility of scaling this system to more complex biological systems.

More specifically, the present invention stems from a series of findings suggesting the existence of yet unexplained but clearly evident interaction between distinct biological entities. This interaction was presently exemplified and characterized by the inventor on the immunological level, showing that exposure of an organism or a sample of cells or tissues (i.e. biological entity) to another biological entity leads to manifestation of certain measurable immunological outcomes, e.g. counts of cells expressing cluster differentiation (CD) markers, levels of circulating cytokines and other markers of inflammation such as AST and ALT. This surprising interaction was first demonstrated between immunologically compromised animals and exogenous samples of lymphocytes, autogenetic as well as syngeneic, and was further reproduced in a recognized model of immune-mediated liver damage in vivo. Further, using the above animal model the inventor demonstrated that it is possible to intervene in this interaction by subjecting one of the biological entities to a stimulus (referred to herein as a triggered entity or entities), e.g. an immuno-modulator such as Dexamethasone, and thereby affecting the immunological outcomes in the other biological entity (referred to herein as the target entity or entities). In other words, the inventor has demonstrated that the nature and the direction of this interaction can be measured and controlled in vivo, and thus may be potentially applicable for diagnostic and therapeutic purposes.

More specifically, the inventor found that immunological outcomes of an exogenous sample of lymphocytes are significantly affected by exposure thereof to immunologically compromised animals, i.e. animals subjected to splenectomy and/or fasting. Most notably, with no apparent physical contact between lymphocyte samples and immuno-compromised animals, the exposed samples had significantly altered levels of CD markers and circulating cytokines compared to unexposed samples (FIGS. 1-3), including autogeneic as well as syngeneic lymphocytes (FIG. 1). Basing on these findings the inventor hypothesized the existence of optional waveform transmission, specifically, radiation transfer between distinct biological entities that surpass the trivial biological effects governed by physical contact or mediators of physical contact between components of biological entities.

Originality of this concept should be more over appreciated in the context of the immune system, as until these findings there were no evidence for ability to induce immune response without direct association between the immune system various components and mediators. More notably, until these findings there were no evidence for immune interaction between an organism and an exogenous sample of lymphocytes without direct association between the two biological entities. These findings provide first evidence that such immune interaction exists and is responsive to immunological triggers, e.g. splenectomy and fasting. One possible explanation of the observed phenomenon can be found in the field of radiation physics. It stems from the notion that many biological processes involve conversion of energy into forms that are probabilistic in nature, wherein light absorption, formation of excited electronic states, transfer of excitation energy, and transfer of electrons and protons exist in more than one state.

Thus, according to the present inventive concept an immunological stimulus can be transferred between distinct entities, specifically, biological entities, with no direct association and no transfer of mediators between the two, and applying terms of waveform transmission, specifically, radiation, immunological states of distinct biological entities are entangled. One of the direct applications of this concept is at a diagnostic level, wherein by evaluating the immunological state of one biological entity one can deduce an immunological state of the other entity, be it a population of cells, organs or organisms. Support for such diagnostic application can be found in Example 1, wherein lymphocyte samples exposed to animals subjected to splenectomy were distinct from those exposed to fasting or control animals. Yet another application of this concept is at a therapeutic level, wherein an immunological state of one biological entity can be modulated or controlled by exposing the other biological entity to a stimulus, e.g. an immunological stimulus in a form of a drug such as Dexamethasone.

Support of these two clinical applications can be found in Example 2, wherein the inventor has further demonstrated that indirect transfer of information between immunological states exists in vivo on the level of whole organisms and may be influenced by exposure of one of the organisms to an immunological stimulus, as hypothesized above. Specifically, using specific markers of inflammation in a recognized animal model of immune-mediated liver damage, the inventor demonstrated that naïve mice manifest higher indices of inflammation when exposed Con A mice compared to non-exposed mice (FIG. 4) and that exposure of untreated Con A mice to Con A mice treated with Dexamethasone had significant palliative effects on indices of inflammation (FIG. 5). Yet again, these findings can be interpreted on diagnostic and therapeutic levels, wherein disease severity of one organism may be evaluated in another organism and can be further ameliorated by immune-modulating this other organism.

Figure 6:
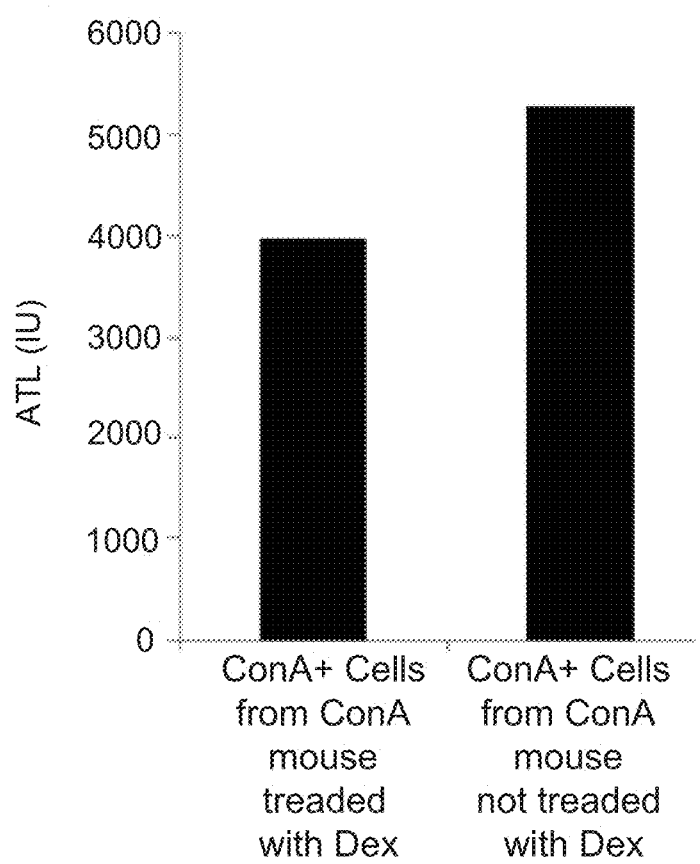
FIG. 6 shows the effect of exposure to samples of splenocytes harvested from Dexamethasone treated donors on disease severity in vivo in the same model, comparing serum ALT levels (IU) in Con A mice exposed to splenocytes harvested Con A donors treated or untreated with Dexamethasone (N=6 in each group) (p<0.05).
Figure 7:
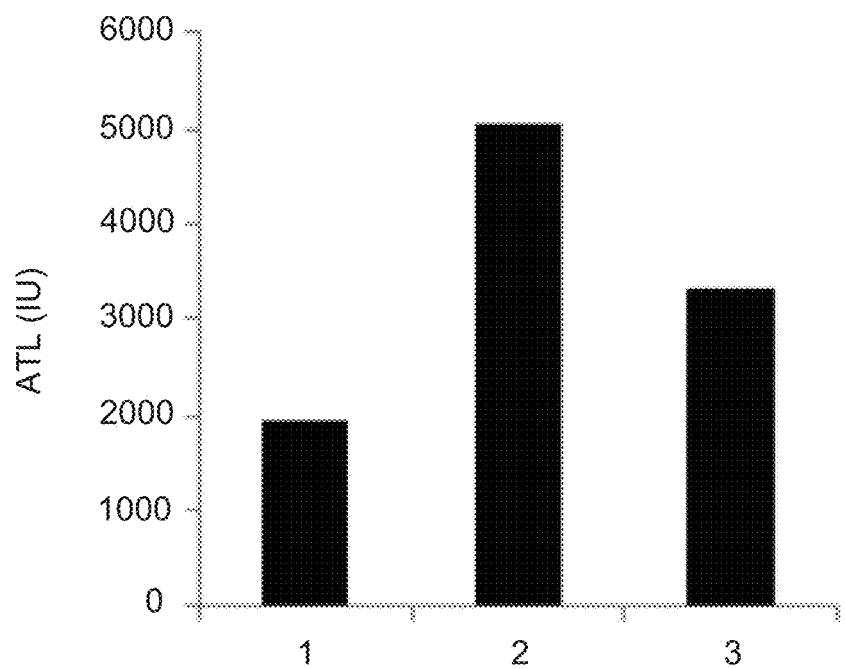
FIG. 7 shows the effect of exposure of Con A mice to splenocytes harvested from Con A donors treated with Dexamethasone (group 1) vs. healthy tissues, whole spleen (group 2) and liver (group 3) (N=6 in each group), comparing serum ALT levels (IU) (p<0.05).

Still further, in Example 3 the inventor demonstrated that the concept of indirect transfer of information between immunological states can be incorporated into a multi component system including biological and potentially non-biological entities in a form of whole organisms, organs and samples of population of cells, which can be used for diagnostic or therapeutic applications. Most notably, the inventor demonstrated that palliative effects of out-of-body Dexamethasone treatment were evident even when Con A mice were exposed to samples of splenocytes from donors treated with Dexamethasone (FIGS. 6 and 7). However, it also became apparent that these observed effects are still need to be interpreted on the level of individual animals due to significant inter-individual variability.

Still further, as demonstrated in Example 4, a study in humans determined the effect of sleep deprivation on possible information transfer from the human to out of body lymphocytes. As describe below, each volunteer was tested twice under condition of normal sleep and of sleep deprivation. A comparison was performed between a tube containing autologous lymphocytes that was kept in the pocket of the volunteer for 24 hours following a sleep deprivation and a similar tube from the same individual under normal sleeping hours. Table 4 summarizes the comparison of A3 to B3 in three volunteers that participated in the trial. A decrease in CD4+CD25+ and in CD8+CD25+ cells was seen in all patients comparing A3 to B3, along with an increase in the CD4/CD8 lymphocyte ratio. The data suggest a long distance effect on out of body lymphocytes that "sense" whether the subject has sleep deprivation or not, thus implying an out of body transfer of information. More importantly, the results demonstrate an indirect and non-invasive transfer of information between biological entities in the systems provided herein.

Information transfer between systems is a developing field which is turning from theory to practice and may be a tool that can be used in biology. The system described in the present invention provides a robust model for biological applications of information transfer in immunological systems. However, it should be appreciated that the model demonstrated here could also be used as an elementary constituent information transfer in variety of other and more complex biological systems.

The Examples characterize a system in which information is transferred between two separate components of the immune system without transfer of observed mediators, and supports the presence of interchange states in isolated immune systems. These results are expected to shed light on the development of schematic models in which different triggers are studied to induce an effect on expression of cell membrane epitopes and cytokine secretion from autogeneic and syngeneic lymphocytes.

The invention provides a platform for the notion that optimal function of the immune system may require an alliance between "classical" immunology, and "wave-based" or "non-direct" immunology. The invention also enables the understandings of several not fully understood biological phenomena, including inter-immune cells interactions, brain-organ connections, out-of-body environmental effects, genotype-phenotype interfaces, organism-host interactions, and placebo effects. These concepts may be applicable for developing methods for both diagnosis and treatment using non classical-based immunotherapy. It may enable performance of diagnostic or therapeutic procedure on out of body autogeneic or syngeneic tissue or organism.

Under the "classical" paradigm for information transfer in biology, the measurement process itself may irreversibly affect the system under study. In the present schematic model, trigger acting on the sender, the entity or the triggered entity (a cell, or other component of the immune system) may enable a specific state to be recovered at the recipient (lymphocyte or cytokine-secreting cell) by traversing the space between them. It is anticipated that the sender performs a measurement between a particle of his state and a particle prepared in a state which he wants to send to the receiver. After these states are confirmed by the heralding event, a pulse of immune information will transform the state of the target part of the immune system into a different one.

In biological systems different levels of "readiness states" may occur, which might depend on the degree of comparison and/or correlation between donors and recipients that act simultaneously on various components of the immune system. Environmental triggers maybe required to start and/or optimize a process. Transfer of information by delivery of an "immunology qubit" may be determined by a trigger occurring in the sender, affecting a constituent of the immune system of the recipient at distance without knowing it. Biological systems are not isolated, and environmental triggers may be fundamental for determining some of the noted effects. The combination of a "readiness state" in which the system exist in, with an environment trigger maybe of higher relevance for biological systems. A simultaneous or in tandem bidirectional "information qubits" transfer between a sender and a recipient may underline the effects expected in these studies.

Information transfer between components of the immune system via a non-direct effect was shown in an isolated system. The described experiment showed that mammalian subjects, such as a mouse or a human can affect cells at a distance and alter the expression of surface markers and cytokine secretion after three types of triggers: fasting, splenectomy, or sleep deprivation. The described laboratory setting does not enable the inventors to detect a wave state by itself; instead, only the measured observables, which are the end result of this effect, were detected. These may be determined for example in the experiments where all tubes are kept under metal shields. The data supports transfer of information between components of the immune system via a non-direct effect. This "non-classical" type of information transfer may serve as a useful tool for immune information processing without transfer of "classical" signals.

In the present schematic models, trigger acting on the sender or the triggered entity (a cell, or other component of the immune system) allows for recovery of the new state at the recipient entity, the target entity (lymphocyte or cytokine-secreting cell) because information traverses the space between the sender and the recipient entities. In biological systems, different levels of "associated states" may occur, and these levels might depend on the degree of comparison and/or correlation between donors and recipients that act simultaneously on various components of the immune system.

The transfer of information via the delivery of an "immunology wave" may be initiated by a trigger that occurs in the sender entity (a triggered entity, a component of the immune system in a splenectomized mouse, a fasting mouse, or following sleep deprivation in humans); the wave affects a constituent of the immune system of the recipient entity at a distance without knowing it. Still further, it should be noted that biological systems are not isolated, and environmental triggers may underlie some of the noted effects. The combination of a wave with an environmental trigger, thus may be relevant to biological systems. A simultaneous or in tandem transfer of bidirectional waves between a sender and a recipient has not been described and may underline the effect noted in the isolated system described in the present invention.

The effect that underlies the outcome noted in the present study on autogeneic cells can be explained by an inherit association between two component of the immune system, suggesting an undefined "historical correlation" between the two parts of the immune system. At the same time, the noted effects on syngeneic cells suggest a "wave-dependent phenomenon" between foreign components of the immune system.

The fidelity obtained in the current schematic model, shows the excellent adherence of properties of information transfer when targeting the expression of cell membranes epitopes and the cytokine secretion of lymphocytes. The results from each mouse and each subject in the described system suggest an inherent pattern that repeats itself. Each attempt for each participant is viewed independently of all others. The use of a standard trigger, enables the protocol used in the present invention to succeed without filtering of the results, and the effects occurred fairly reliably. The mice experiments described were repeated in an independent laboratory, further supporting the feasibility of setting up isolated conditions under which these effects can be measured.

The lack of the expected effects for all parameters in all experiments and the changes in opposing directions for some of the measured observables may result from the disordered nature of immune pathways and from multiple confounding factors that act simultaneously and are hard to control. These factors are inherent to any biological system. Nonetheless, the out-of-body information transfer in one direction was significant for several of the tested parameters in repeated testing. For some of the observables, the changes were small and could be claimed to result from intra-test variability. Each mouse was tested in a separate cage, and only those parameters that changed in two separate experiments were used for the final data analysis; thus, the results support a yet to be defined electromagnetic wave effect.

Still further, the results described in the present study support the presence of wave repeaters with built-in memory in an isolated system, which is mandatory for long-distance communication. Although the memory in immune systems is based on the direct delivery of mediators or messenger molecules secreted by immune cells, a "wave type-memory" is required at both the transmitting and receiving sites (or entities in the context of the present disclosure) for the propagation of information. This memory can underline some of the observed measures in the present invention.

By enabling diagnostic and therapeutic procedures to be performed on out-of-body autogeneic or syngeneic tissue or organisms, these concepts may be applicable to the development of methods for both diagnosis and treatment using teleportation-based immune therapy.

From a broader perspective, the present invention provides methods and systems for transferring immunological information between a plurality of biological and non-biological entities in a non-direct way. As presently exemplified, these methods and systems can operate under ambient temperature, pressure and lighting. Although the underlying mechanism of this kind of immunological information transfer is not clear yet, the immunological outcomes of the methods of the invention are clearly measurable on the cellular and molecular levels.

It is conceived that methods and systems of the present invention are highly flexible and are not limited by the number of biological entities, be it organisms, organs, tissues or population of cells. It is also conceived that apart from biological entities, methods and systems of the invention may also involve non-biological entities for augmenting transfer immunological information or for measuring immunological states of biological entities. Further, methods and systems of the invention can incorporate additional agents used for diagnostic or therapeutic purposes. It is further conceived that transfer of immunological information by methods and systems of the invention can involve any biological entity, be it organisms, organs, tissues or population of cells, and is solely contingent upon diagnostic or therapeutic purposes of this transfer. In other words, any entity can serve as a recipient of immunological information and also as a transmitter of immunological information (the target entity) depending on diagnostic or therapeutic application, respectively. Still further, it is conceived that methods and systems of the invention can involve biological entities represented by organisms, organs, tissues or population of cells that are autogenetic or syngeneic, from the same and different species.

Further, this invention can be potentially scaled to more complex systems incorporating additional methods and tools, which might in turn lead to a better understanding of functionality of the immune system and its various components.

The effects demonstrated in the present EXAMPLES may be dependent of electromagnetic radiation or any other type of radiation or of transfer of energy and may be explained by any type of physical or chemical or any other wave phenomenon. Independent of the mechanism underlying these demonstrated effects, the inventive concept behind the present invention is rather how to use this mechanism, being it a radiation as electromagnetic radiation, voice radiation, light radiation, or any other type of radiation, for modulating or controlling physiological conditions and pathologies.

The world is naturally radioactive and approximately 82% of human-absorbed radiation doses, which are out of control, arise from natural sources such as cosmic, terrestrial, and exposure from inhalation or intake of radiation sources. In recent years, several international studies have been carried out, which have reported different values regarding the effect of background radiation on human health. Gamma radiation emitted from natural sources (background radiation) is largely due to primordial radionuclides, mainly (232) Th and (238) U series, and their decay products, as well as (40)K, which exist at trace levels in the earth's crust. Their concentrations in soil, sands, and rocks depend on the local geology of each region in the world. Naturally occurring radioactive materials generally contain terrestrial-origin radionuclides, left over since the creation of the earth. In addition, the existence of some springs and quarries increases the dose rate of background radiation in some regions that are known as high level background radiation regions. The type of building materials used in houses can also affect the dose rate of background radiations.

Gamma rays, X-rays and the higher energy range of ultraviolet light constitute the ionizing part of the electromagnetic spectrum. The lower-energy, longer-wavelength part of the spectrum including visible light, infrared light, microwaves, and radio waves is all non-ionizing, that mainly cause heating when interacting with tissue. Although the part of the ultraviolet spectrum that penetrates the Earth's atmosphere is non-ionizing, this radiation does far more damage to many molecules in biological systems than can be accounted for by heating effects, with sunburn being a well-known example. These properties derive from the power of ultraviolet to alter chemical bonds, even without having quite enough energy to ionize atoms.

Radiation refers to the phenomenon of waves radiating (i.e., traveling outward in all directions) from a source. This aspect leads to a system of measurements and physical units that are applicable to all types of radiation. Because such radiation expands as it passes through space, and as its energy is conserved (in vacuum), the intensity of all types of radiation radiating from a point source follows an inverse-square law in relation to the distance from its source. Electromagnetic radiation (EM radiation or EMR) is a form of radiant energy released by certain electromagnetic processes. Visible light is one type of electromagnetic radiation, other familiar forms are invisible electromagnetic radiations such as X-rays and radio waves. Classically, EMR consists of electromagnetic waves, which are synchronized oscillations of electric and magnetic fields that propagate at the speed of light. The oscillations of the two fields are perpendicular to each other and perpendicular to the direction of energy and wave propagation, forming a transverse wave. Electromagnetic waves can be characterized by either the frequency or wavelength of their oscillations to form the electromagnetic spectrum, which includes, in order of increasing frequency and decreasing wavelength: radio waves, microwaves, infrared radiation, visible light, ultraviolet radiation, X-rays and gamma rays. Electromagnetic waves are produced whenever charged particles are accelerated, and these waves can subsequently interact with any charged particles. EM waves carry energy, momentum and angular momentum away from their source particle and can impart those quantities to matter with which they interact. Quanta of EM waves are called photons, which are mass less, but they are still affected by gravity. Electromagnetic radiation is associated with those EM waves that are free to propagate themselves ("radiate") without the continuing influence of the moving charges that produced them, because they have achieved sufficient distance from those charges. Thus, EMR is sometimes referred to as the far field. In this jargon, the near field refers to EM fields near the charges and current that directly produced them, as (for example) with simple magnets, electromagnetic induction and static electricity phenomena [9, 10].

The effects of EMR upon biological systems (and also many other systems, under standard conditions) depend both upon the radiation's power and its frequency. For EMR of visible frequencies or lower (i.e., radio, microwave, infrared), the damage done to cells and other materials is determined mainly by power and caused primarily by heating effects from the combined energy transfer of many photons. By contrast, for ultraviolet and higher frequencies (i.e., X-rays and gamma rays), chemical materials and living cells can be further damaged beyond that done by simple heating, since individual photons of such high frequency have enough energy to cause direct molecular damage. The transfer of waves between systems, or the type of energy being transferred between systems is another aspect of this invention.

Any type of wave coming out of any type of radiation may be involved in the noted effect. Electromechanical radiation or any type of radiation coming from voice or light may contribute to the generation of the wave. A combination between several types of radiation may also exist [11, 12].

Various techniques are employed to determine the amounts, retention, and distribution of radioactivity in human subjects in vivo. The principal method is gamma-ray spectrometry with large NaI(Tl) scintillation crystals ("whole-body counting"). When a sufficient amount of radioactivity is present in a subject, scanning techniques assist in determining its distribution in the body. Specialized instruments such as a xenon-filled proportional counter and a dual-crystal (phoswich) detector are used to measure low-energy photon emitters, primarily plutonium and americium. americium. The observed gamma rays result from the decay of 214Bi (RaC) and 208Tl (ThC"), respectively. Since each of these nuclides is preceded in the decay chain by an isotope of the noble gas radon, some of which is exhaled, its activity is not equal to that of the parent radium or thorium. Therefore, breath samples are collected to determine the exhalation rate of the precursor isotope, 222Rn (radon) or 220Rn (thoron). The total body content is then the sum of the gamma activity and the exhaled radioactivity, referred to as the retained and emanating fractions, respectively [13].

All objects, including human bodies, emit electromagnetic radiation. The wavelength of radiation emitted depends on the temperature of the objects. Such radiation is sometimes called thermal radiation. Most of the radiation emitted by human body is in the infrared region, mainly at the wavelength of 12 micron. The wavelength of infrared radiation is between 0.75 to 1000 micron (1 micron=$10^{-6}$ meters). The amount of thermal radiation emitted by an object depends on its surface temperature, area and characteristics. Warmer object emits more thermal radiation than cooler one.

The present invention may be also interpreted within the field of bioelectromagnetics, also known as bioelectromagnetism or magnetobiology, referring to interaction between electromagnetic fields and biological entities. Specifically, referring to electrical or electromagnetic fields produced by living cells, tissues or organisms, for example, the cell membrane potential and the electric currents that flow in nerves and muscles, as a result of action potentials. More specifically, magnetobiology refers to biological effects of mainly weak static and low-frequency magnetic fields less than about 0.1 millitesla (or 1 Gauss) and 100 Hz, which do not cause heating of tissues. Magnetobiological effects have unique features that distinguish them from thermal effects. Magnetobiological effects may be observed for alternating magnetic fields just in separate frequency and amplitude intervals, and also for simultaneously present static magnetic or electric fields depending on their polarization. Electromagnetic and magnetic fields may be produced by biological organisms and sensed by organisms, a phenomenon known as magnetoreception. An example of magnetobiological effects is the magnetic navigation by migrant animals and birds, wherein it was established that some organisms are able to detect small variations of the geomagnetic field on the order of tens of nanoteslas to find their seasonal habitats.

Of particular relevance to the present context is an accumulating evidence demonstrating that non-thermal exposures of cells of the immune system to extremely low frequency electromagnetic fields (<300 Hz) can elicit cellular changes that are relevant to in vivo immune activity. A similar responsiveness to nonionizing electromagnetic energy in this frequency range has also been documented for tissues of the neuroendocrine and musculoskeletal systems. Although the knowledge about the underlying mechanism by which such low frequency electromagnetic fields can induce cellular changes is still very limited, it is generally believed that the cell membrane- and $Ca^{2+}$-mediated signaling may play part in the inductions of these cellular field effects.

Regardless of the fact that the exact mechanism underlying the nature of transfer of immunological information between biological entities is still unclear, existence of such transfer of immunological information and implementation thereof were clearly demonstrated in the presently given Examples 1 to 3. Thus, for diagnostic and therapeutic purposes a controlled and directed transfer of immunological information can be conceptualized between different entities, including specifically, biological and also non-biological entities.

More specifically, in a first aspect, it is conceived that the present invention provides a method for modulating a physiological state of, or inducing a physiological effect on a target biological entity by exposing said target entity to a single or a plurality of triggered entities. More specifically, the method comprising in a first step (a) providing a single or a plurality of other entities, wherein at least one of said other entities is a biological entity. The next step (b), involves subjecting at least one of said other entities to a trigger. In some specific embodiments, the exposure of said entity to a trigger or stimulus may be performed for a selected time period under suitable conditions. The next step (c) involves exposing the target entity to at least one of the triggered entity obtained in (b), thereby modulating a physiological state of the target biological entity. In some specific embodiments, the step of exposing the target entity to at least one other triggered entity, enables transformation of information between the entities in an indirect a non-invasive manner. In some specific embodiments, such indirect and non-invasive manner for information transfer between the entities, does not require and contact or transfer of molecules between said entities.

It should be appreciated that in the present disclosure a trigger acting on the sender entity (also referred to herein as a triggered entity), which can be according to certain embodiments, any subcellular organelle or molecule, any type of a cell, or other component of the immune system or of any other biological system, or any organ, or whole body, from the same or from a different species compared to the recipient entity (also referred to herein as the target entity), to allow information to be recovered at the recipient or target entity by traversing the space between them. In yet some further embodiments, the target entity may be any subcellular organelle or molecule, any type of a cell, or other component of the immune system or of any other biological system, or any organ, or whole body, from the same or from different species compared to the sender (triggered) entity.

Biological systems are not isolated, and environmental triggers may be fundamental for determining some of the noted effects. A simultaneous or in tandem bidirectional transfer of information between a sender and a recipient entities was not described in radiation physics, and may underline the effect noted in the isolated system described in the present study.

In this connection, one should appreciate that the term "biological entity" refers to any biological organism or any part thereof, i.e. a tissue, an organ or a population of cells of the same or heterologous origin or species. For the purpose of specific embodiments, the biological entity refers to a mammalian organism or part thereof. For the purpose of other embodiments, the biological entity is a human organisms, also referred to herein as a subject, or a part thereof.

Thus, the above methods of the present invention may involve biological entities that are at least one of an organism, an organ, a tissue, a cell, a sub-cellular component or a cellular fraction.

Further, the above method of the invention factually involves a plurality of biological entities, more specifically at least two biological entities or any parts thereof, which are of the same or from heterologous origin or species, or any combination thereof.

By the term "single or plurality" when relating to entities, biological entities or triggered entities as define herein it is referred to at least one, two, three, four, five, six, seven, eight, nine, ten or more entities, biological entities or triggered entities. More specifically, the methods or the invention, as well as the system described herein after refer to the use of plurality of entities. The term "plurality", as used herein is meant being plural, specifically, more than one, that may in some embodiments include two or more, three, four, five, six, seven, eight, nine, ten or more, specifically, 11, 12, 13, 14, 15, 16, 17, 18, 19, 20, 21, 22, 23, 34, 25, 26, 27, 28, 29, 30, 31, 32, 3, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or more entities, specifically, 100, 150, 200, 250, 300, 3450, 400, 450, 500, 550, 600, 650, 700, 750, 800, 850, 900, 950, 1000 or more.

In other words, biological entities to which methods of the present invention are applicable may comprise a target biological entity and said at least one other biological entity (being the triggered entities) which is of an autogeneic, allogenic, syngeneic or xenogeneic source to the target biological entity. In this connection, the terms autogeneic and allogeneic are borrowed from the context of grafts; autogeneic refers to a tissue or organ of the same individual; allogeneic is a genetically distinct tissue or organ because of being derived from another individual of the same species; syngeneic is genetically identical, or sufficiently identical and immunologically compatible because of being derived from the same species; xenogeneic refers to derived from a different species and therefore genetically and immunologically distinct.

Further in the context, at least one of the biological entities is a target biological entity that is herein defined as an organism or a part thereof wherein a desirable effect is sought, e.g. modulation of a physiological state or reduction of inflammation and related clinical conditions associated therewith, which can include infection, trauma or cancer. In this context, the term "other" in the context of a biological entity is a non-target biological entity (also referred to herein as a triggered biological entity) that is an organism or a part thereof subjected to a trigger or a plurality of triggers to achieve the desirable immunological outcome, that may include in specific and non-limiting examples, irradiation, magnetic field and therapeutic compositions.

It should be appreciated that a target and a non-target or triggered biological entities may also comprise a group of biological entities or parts thereof. It is further contemplated that due to the radiation nature of interaction between the two biological entities, the non-target biological entity wherein a trigger is introduced can be replaced with non-biological entity, e.g. in the form of a computer and an algorithm, acting on the target biological entity by means of radiation. For the purpose of specific embodiments, methods of the invention may further comprise a plurality of non-biological or any combination thereof and non-target biological entities.

In certain embodiments said target biological entity is a human subject in which a desirable immunological effect is sought, e.g. treatment of inflammation or cancer.

In yet other embodiments, said target biological entity is a tissue or population of cells of the same or heterologous origin or species, which is subjected to a desirable immunological effect, e.g. reduction of certain populations of cells such in bone marrow transplantations.

As indicated above, the present invention provides a method for modulating a physiological state of, or inducing a physiological effect on a target biological entity by exposing said target entity to a single or a plurality of triggered entities. The term "physiological state" is used herein in a broad sense and refers to the condition or state of the body or any parts or organs thereof or bodily functions.

In certain embodiments, the physiological state modulated by the method of the invention may be at least one of immunological state, metabolic state, physical state and chemical state.

In yet some embodiments, modulation of the physiological state of the target entity by the triggered entity is enabled by at least one waveform transmission that exists between the single or a plurality of triggered entities and the target entity. In more specific embodiments waveform transmission may be at least one of electromagnetic radiation, radio waves, sound waves, microwaves, infrared radiation, visible light, ultraviolet radiation, X-rays, and gamma rays.

More specifically, the term "wave" as used herein, is an oscillation accompanied by a transfer of energy that travels through space or mass. Wave motion transfers energy from one point to another, which may or may not displace particles of the transmission medium, that is, with little or no associated mass transport. There are two main types of waves, mechanical waves propagate through a medium, and the substance of this medium is deformed. The deformation reverses itself owing to restoring forces resulting from its deformation. For example, sound waves propagate via air molecules colliding with their neighbors. When air molecules collide, they also bounce away from each other (a restoring force). This keeps the molecules from continuing to travel in the direction of the wave. The second main type of wave, electromagnetic waves do not require a medium. Instead, they consist of periodic oscillations of electrical and magnetic fields generated by charged particles, and can therefore travel through a vacuum. These types of waves vary in wavelength, and include radio waves, microwaves, infrared radiation, visible light, ultraviolet radiation, X-rays, and gamma rays.

A wave can be transverse or longitudinal. Transverse waves occur when a disturbance creates oscillations that are perpendicular to the propagation of energy transfer. Longitudinal waves occur when the oscillations are parallel to the direction of energy propagation. While mechanical waves can be both transverse and longitudinal, all electromagnetic waves are transverse in free space.

It should be appreciated that due to the wave and/or transfer of energy nature of interaction between biological and non-biological entities, there is no requirement for direct contact or any limitations with regard to the minimal or maximal distances between the entities, biological and non-biological entities. In other words, in certain embodiments, the interaction between the target and the triggered entities may be transmitted or teleported by means of any type of waveform transmission or any type of energy, be it electron tunneling or low frequency electromagnetic fields, static or alternating, also referred to as non-thermal and non-ionizing electromagnetic fields. Therefore by the term "exposing" in the context of the target triggered non-target entities it is meant that these entities are placed or situated at a certain distance one from the other, as detailed below. It should be appreciated however, that in certain embodiments, no physical direct contact between the entities exists.

Still for the purpose of certain embodiments it may be desirable that the minimal distance between entities is of 0.00001 nm or greater. In yet some other embodiments, the different entities are placed in a distance of between 0.00001 nm or less, to about 100,000 km or more. In yet some other embodiments, the distance between the entities may be in the range of Angstroms, nanometers, micrometers, millimeters, centimeters, meters, kilometers, miles or more. In some specific embodiments, the distance may range between about 0.00001 nm to about 1 km, between about 0.00001 nm to about 100 meter, 90 meter, 80, 70, 60, 50, 40, 30, 20 10, 9, 8, 7, 6, 5, 4, 3, 2 and 1 meter. In yet another embodiment, the distance may be about 1 nm or more, 10 nm or more, 100 nm or more, 1 micrometer or more, 1 millimeter or more, 1 centimeter or more, 2, 3, 4, 5, 6, 8, 9, 10, 11, 12, 13, 14, 15, 16, 17, 18, 19, 20, 30, 40, 50, 60, 70, 80, 90 and 100 cm or more.

In some specific embodiments, the methods of the invention are particularly applicable for modulating immunological state (also immunological status) of the target biological entity, namely in specific embodiments the physiological state is an immunological state.

In this context an immunological state encompasses any number of immunological features which reflect physiological functioning of the immune system in both, health and disease, including a disease induced by extrinsic as well as intrinsic or inherent causes (e.g. infectious agents or cancer). In the present context a disease associated with an immunological state can be also interpreted as an immune-compromised state of an organism or parts thereof and therefore includes conditions such as autoimmune diseases, hypersensitivities, immune deficiency, transplant rejection. Further, the term "immunological state" as meant herein refers to any number of the physical, chemical, biochemical or molecular characteristics of the components of the immune system in vitro, in situ and in vivo, as reflected in circulating components of the humoral and cell-mediated immune responses as well as histological characteristics of the primary lymphoid organs of the immune system, i.e. the thymus and bone marrow, and secondary lymphatic tissues such as spleen, tonsils, lymph vessels, lymph nodes, adenoids, and skin and liver. At least in vertebrates, characteristics of the circulating components can usually be evaluated by testing blood samples, and immune system organs—can be surgically excised for examination while an organism is still alive. Sill further, the term immunological state as meant herein refers to any number of components or direct and in direct mediators, and markers of the innate immune system as well as acquired or adaptive immune system.

The term "metabolic state" or "metabolism" refer to all of the body's chemical processes, the digestion of food, and the elimination of waste, namely the entire range of biochemical processes that take place in living organisms. Metabolism consist of both catabolism and anabolism which are the buildup and breakdown of substances, respectively.

The term "physical state" as herein defined should be taken to mean in its broadest sense and relates to the overall state or condition of the target biological entity. Physical state may be evaluated or refer for example to temperature, blood pressure, as well as to sugar level, lipid level, different metabolite level, hormones, enzymatic activity and the like.

The term "chemical state" as used herein refer to the level and composition of different chemical compounds in the specific biological entity, specifically the target entity. In case the target entity is an organism, for example, a mammalian subject, the chemical state referred to herein may indicate the state and/or level of different chemical compounds in the target entity or in any sample thereof, for example body fluids of the target entity, being a subject. In some specific embodiments, the chemical state may refer to the level or composition of different chemical compounds that may be evaluated using a chemistry screen of a blood sample of said subject indicating the levels of different protein compounds, for example, albumin, Alkaline Phosphatase, Alanine Aminotransferase (ALT), Aspartate Aminotransferase (AST), Bilirubin (total and direct), Blood Glucose, blood Urea Nitrogen, Calcium (Ca) in Blood, Carbon Dioxide (Bicarbonate), Chloride (Cl), Cholesterol and Triglycerides, Creatinine and Creatinine Clearance, Gamma-Glutamyl Transferase (GGT), Lactate Dehydrogenase, Phosphate in Blood, Potassium (K), Sodium (Na), Total Serum Protein, Uric Acid and the like.

In this connection, the term "modulating" encompasses both, the reduction as well as augmentation of any number of physiological (e.g. immunological) features referred to above. More specifically, as the immunological states of the target and the trigger entities which show indirect transfer of information between them, methods of the invention may be applied to decrease or increase any number of immunological factors in the target entity by introducing a trigger to the non-target entity. In this context, said reduction or decrease may be expressed in terms of at least about 1%-100%, about 5%-95%, about 10%-90%, about 15%-85%, about 20%-80%, about 25%-75%, about 30%-70%, about 35%-65%, about 40%-60% or about 45%-55% with respect to the extent of the same immunological features prior to triggering. It may be also expressed in terms of at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or about 100% reduction or decrease with respect to the extent of the same immunological features prior to triggering.

In the same way, said augmentation or increase may be expressed in terms of at least about 1%-1000%, about 5%-95%, about 10%-90%, about 15%-85%, about 20%-80%, about 25%-75%, about 30%-70%, about 35%-65%, about 40%-60% or about 45%-55%, or at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 100%, 200%, 300%, 400%, 500%, 600%, 700%, 800%, 900% or about 1000% with respect to the extent of the same immunological features prior to triggering.

Still further, when referring to a trigger introduced in, or applied to, a non-target biological entity (a triggered entity or the sender) it is meant any type of trigger which has a direct or indirect impact on the immunological state of said target. In some embodiments, these types of triggers may be referred to as immunological triggers. Relying on the concept of indirect information transfer between immunological states, it is conceived immunological triggers are teleported from the non-target to target biological entity and may be further modulated by one or more non-biological entities.

Thus, for the purpose of specific embodiments said trigger is an electronically induced trigger, optionally controlled by an algorithm, or another method.

Yet in other embodiments, the trigger may be a physical trigger or a plurality of physical triggers, which may include exposure of the non-target entity to a certain temperature, irradiation of certain frequency and intensity and low electromagnetic radiation.

For the purpose of further specific embodiments, such physical triggers may include exposure to temperature in the range of −300° C. or less to +300° C. or more, for any length of time. Specifically, −300, −250, −200, −150, −100, −90, −80, −70, −60, −50, −40, −30, −20, −10, −9, −8, −7, −6, −5, −4, −3, −2, −1, 0, 1, 2, 3, 4, 5, 6, 7, 8, 9, 10, 20, 30, 40, 50, 60, 70, 80, 90, 100, 150, 200, 250, 300° C. or more.

Yet in other embodiments, a physical trigger may be in a form of electromagnetic radiation in the visible spectrum range, corresponding to about 390 to 700 nm or to 430-790 THz.

In other specific embodiments, said electromagnetic radiation may of an extremely low frequency such as <300 Hz, as previously mentioned such electromagnetic field of this nature have been particularly associated with immunological effects.

For the purpose of specific embodiments, physical insult may be directly or indirectly induced on a non-target entity, also referred to herein as the triggered entity.

Thus, from a broader perspective, methods of the present invention involve in some embodiments, the exposure of at least one of the non-target entity to an effective amount of at least one trigger which may be any one of physical, chemical, and biological trigger or a therapeutic procedure or any combination thereof.

Physical trigger as meant herein refers to any intervention based on physical forces inflicted on the non-target entity (being the triggered entity), including physical forces acting at a distance such as electromagnetic forces mentioned above or gravitational forces, and also forces acting upon contact such as tension, friction, spring forces and other applied forces.

Chemical trigger refers to any chemical substance (natural or synthetic) that initiates or catalyzes a chemical reaction in the non-target entity, including chemical substances from biological and non-biological sources (e.g. drugs).

For the purpose of specific embodiments, the triggered entity may be exposed to an effective amount of at least one chemical trigger that may be in certain embodiments selected from natural or synthetic compounds, drugs, any preparations, extracts, mixtures and any combinations thereof.

In yet some further specific embodiments, a chemical trigger may involve the exposure of the triggered entity to a chemical compound, for example, Concavalin A, or Dexamethason. Thus, in some embodiments, a chemical trigger may be Con A. Concanavalin A (ConA) as used herein, is a lectin-donut (carbohydrate-binding protein) originally extracted from the jack-bean, *Canavalia ensiformis*. It is a member of the legume lectin family and acts as a plant mitogen.

In yet some further embodiments, a chemical trigger may be Dexamethason. Dexamethasone as used herein, is a steroid medication used in the treatment of inflammatory conditions.

In yet some further embodiments, any chemical product, small molecules, any drug, vitamins, synthetic or natural extracts, specifically, plant extracts may be used as a chemical trigger. Non limiting examples for drugs useful as chemical triggers may include antibiotics, specifically beta-lactams, statins/HMG-CoA reductase inhibitors, inducers or inhibitors of Cytochrom P-450 for example, Acetaminophen (N-(4-hydroxyphenyl)ethanamide, (paracetamol)), Phenobarbital, Phenytoin, Carbamazepine, Primidone, Ethanol, Glucocorticoids, Rifampin, Griseofulvin, Quinine, Omeprazole, Amiodarone, Cimetidine, Erythromycin, Grape fruit, Isoniazid, Ketoconazole, Metronidazole, Sulfonamides, Chlorpromazine, phenylbutazone, halogenated anesthetic agents, sulindac, Dapsone, INH, halothane, amoxicillin-clavulanic acid, phenobarbital, Para-amino salicylate, Clofibrate, Procainamide, Gold salts, propylthiouracil, chloramphenicol, nitrofurantoin, methoxyflurane, penicillamine, paraquat, Tetracycline, Contraceptive and anabolic steroids, rifampin, Aspirin and Sodium valproate. Chemical trigger may further includes any synthetic or natural β-glycolipids, for example, glucosylceramide, monosaccharide ceramide, galatosylceremide, lactosyl-ceramide, gal-gal-glucosyl-ceramide, GM2 ganglioside, GM3 ganglioside and globoside.

Biological trigger refers to an exposure of the entities to any biological trigger, stimulus or element, e.g. viruses, bacteria or fungi or others, acting on the state, specifically, physiological (e.g. immunological) of the non-target biological entity. In this connection, it should be appreciated that as the concept of indirect information transfer between immunological states also applies to the non-target biological entity, thus one may conceive that introduction of a trigger may involve a plurality of exposures of one non-target entity to another non-target ultimately ensuing in modulation of an immunological state in a target biological entity.

Of particular relevance to the present invention are methods in which at least one non-target (triggered) entity is exposed to an effective amount of a biological trigger selected from immunomodulatory compounds, cytokines, hormones, growth factors, antibodies, recombinant proteins, nucleic acid sequences, amino acid sequences or any combination of these compounds administered per se or in a form of a drug.

Under immunomodulatory compound it is meant any compound or composition capable of modifying or regulating one or more immune functions. Examples of such compounds include, although not limited to Immunomodulatory Drugs (IMiDs) that constitute thalidomide class drugs and its analogues, lenalidomide, pomalidomide and apremilast. Another example is Non-steroidal anti-inflammatory drugs (NSAIDs) counteracting the cyclooxygenase (COX) enzyme and thereby preventing the synthesis of prostaglandins and development of inflammation.

Other notable examples of biological triggers, that may involve in certain embodiments immunomodulatory compounds including cytokines, hormones, growth factors, antibodies, recombinant proteins, and polynucleotides and peptides. Cytokines as meant herein refers to a category of small proteins (~5-20 kDa) produced by a broad range of immune cells, e.g. macrophages, B and T lymphocytes and mast cells, as well as non-immune cells, e.g. endothelial cells, fibroblasts, and stromal cells. Cytokines include, although not limited to include chemokines, interferons, interleukins, lymphokines, tumor necrosis factor, but generally not hormones or growth factors important in cell signaling. Cytokines govern the complexity of immune responses in modulating the balance between humoral and cell-based immune responses, and the maturation, growth and responsiveness of particular immune cell populations, some cytokines enhance or inhibit the action of other cytokines in complex ways. Cytokines are different from hormones, which are also important cell signaling molecules, in that hormones circulate in much lower concentrations and hormones tend to be made by specific kinds of cells.

As known in the art the term "hormones" as herein defined refers to natural or synthetic substances that affect the activity of cells usually at sites remote from the origin of the hormones.

Association between hormonal and immune response is well established. Numerous studies have shown that an imbalance in thyroid and adrenal hormones, testosterone, the estrogen's (estrone, estradiol, estriol), and progesterone can affect responsiveness of the immune system. The female sex hormones have been shown to heighten immune response. The adrenal hormone cortisol inhibits the production of prostaglandins and thereby suppresses inflammation. Hydrocortisone (INN, USAN, BAN) is a synthetic cortisol used as an anti-inflammatory medication. Another example of a synthetic glucocorticoid used for the treatment of inflammation is Dexamethasone and its derivatives.

The term growth factor is sometimes used interchangeably with the term cytokine. Among growth factors associated with immunomodulatory effects, the most recognized is the Transforming Growth Factor-beta (TGF-β). The pivotal function of TGF-β in the immune system is to maintain tolerance via the regulation of lymphocyte proliferation, differentiation, and survival. TGF-β also controls the initiation and resolution of inflammatory responses through the regulation of chemotaxis, activation, and survival of lymphocytes, natural killer cells, dendritic cells, macrophages, mast cells, and granulocytes. There is a relatively recent awareness or the role of insulin-like growth factors (IGF-I and II) in the immune response. IGF-I and IGF-IR in particular may represent an important switch governing the quality and amplitude of immune responses, particularly in the pathogenesis of autoimmune diseases.

The relationship between antibodies and immunity is obvious, and therefore, in certain embodiments, immunomodulating agents applicable in the methods of the invention may include antibodies. The term antibody as referred to herein includes whole antibodies and any antigen binding fragment (i.e. antigen-binding portion) or single chain thereof. An antibody refers to a glycoprotein comprising at least two heavy (H) chains and two light (L) chains interconnected by disulfide bonds, or an antigen binding portion thereof. Each heavy chain is comprised of a heavy chain variable region (abbreviated herein as $V_H$) and a heavy chain constant region (abbreviated herein as CH). Each light chain is comprised of a light chain variable region (abbreviated herein as $V_L$) and a light chain constant region (abbreviated herein as CO. The $V_H$ and $V_L$ regions can be further subdivided into regions of hypervariability, termed complementarity determining regions (CDRs), interspersed with regions that are more conserved, termed framework regions (FRs). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system.

The term antigen-binding portion of an antibody, as used herein, refers to one or more fragments of an antibody that retain the ability to specifically bind to an antigen. It has been shown that the antigen-binding function of an antibody can be performed by fragments of a full-length antibody.

An antibody fragment is a portion of an antibody such as $F(ab')2$, $F(ab)_2$, Fab', Fab, and the like. Regardless of structure, an antibody fragment binds with the same antigen that is recognized by the intact antibody. For example, an anti-(polypeptide according to the present invention) monoclonal antibody fragment binds an epitope of a polypeptide according to the present invention. The term "antibody fragment" also includes a synthetic or a genetically engineered polypeptide that binds to a specific antigen, such as polypeptides consisting of the light chain variable region, Fv fragments consisting of the variable regions of the heavy and light chains, recombinant single chain polypeptide molecules in which light and heavy variable regions are connected by a peptide linker (scFv proteins), and minimal recognition units consisting of the amino acid residues that mimic the hypervariable region.

In its further conceived that term immunomodulatory or modulating compound as meant herein also refers to any derivatives, synthetic or recombinant preparations of the above mentioned factors and compounds, including synthetic cytokines and growth factors, synthetic steroids, and prostaglandings (i.e. lipid compounds), and derivatives thereof, as well as recombinant proteins, and polynucleotides and peptides. In this connection, of particular relevance is a novel class of immunomodulatory compounds, Immune Selective Anti-Inflammatory Derivatives (ImSAIDs), which are unrelated to steroid hormones or NSAIDs. ImSAIDs are peptides demonstrated as capable of controlling and modulating inflammation and tissue repair via activation and migration of inflammatory cells (developed by IMULAN BioTherapeutics, LLC).

With respect therapeutic procedures that may be used as a trigger in the methods of the present invention reference is made herein to any type of surgical or non-surgical manipulation or intervention performed on a non-target biological entity. More specifically, these interventions may include, although not limited to, drug therapy (pharmacotherapy, chemotherapy or mesotherapy, i.e. cosmetic therapy), gene therapy, therapy by means of a medical device, chrysotherapy (aurotherapy using gold salts), hormone therapy, biotherapy (e.g. vaccine or phytotherapy), aromatherapy, ozonotherapy, hydrotherapy, and also therapy by any means of energy (electrotherapy, electromagnetic therapy, magnet therapy, phototherapy, radiotherapy), therapy by temperature (thermotherapy or cryotherapy), manual therapy, cymatic therapy, music therapy, and potentially psychotherapy and meditative therapy.

It is further conceived that the non-target entity is exposed to at least one of the above trigger or to a combination thereof under suitable conditions, for example but not limited to the conditions exemplified herein, for a selected time period, which may be from less than a second to years.

In specific embodiments, said therapeutic procedure may comprise surgical manipulations for example, splenectomy, hepatectomy, or any other procedures such as sugar loading, starvation, sleep deprivation and depletion of immune-system components, any type of treatment by administering a drug of any type of a therapeutic measure, or by performing any type of procedure which can affect the biological or the non-biological entity in a beneficial of deleterious effect.

In other words, the triggered entity or entities in accordance with the present disclosure may be subjected to the trigger by means of applying at least one of, a physical (for example but not limited to a certain temperature, radiation, etc.), chemical (for example but not limited to administration of natural or synthetic compounds, extracts or any combinations thereof), or biological trigger (for example but not limited to administration of imuno-modulatory compounds, cytokines, hormones, growth factors, antibodies, recombinant proteins, nucleic acid sequences, amino acid sequences and any combinations thereof) or by means of applying a therapeutic procedure (for example but not limited to surgical manipulations, sugar loading (namely saturating amounts of consumed sugars resulting in an increase in body glucose level), starvation, sleep deprivation and depletion of immune-system components).

A model using a non-natural computer-brain interface for induction of an out of body effect was described showing a non-invasively transfer of information between brains of different species[8]. Translation of human volunteer's intention to stimulate a rat's brain motor area responsible for tail movement was shown. The data suggested feasibility of a computer-mediated brain-brain interface to link neural functions between two biological entities. The presently disclosed data confirms a computer interface-independent out of body transfer of information but does not rule out of using a computer or any other type of non-biological measure to be associated with the communication of the information.

Thus, in yet some other embodiments, the method of the present invention may further comprise the step of providing at least one additional mediating element placed between said target and at least one other non-target biological or non-biological entities (the triggered entities). In particular cases, said mediating element may be a device, computer, medical device or any surface or element.

It should be appreciated that in certain embodiments, the additional element cannot be an energy source that amplifies and extends the information transmitted between the entities.

Thus, in certain embodiments, the method of the invention further comprise the step of providing an additional mediating element between the target entity and at least one of the triggered entities, provided that said mediating element is not an energy source or an energy amplifier.

It is further conceived that in specific embodiments, the target biological entity is a subject suffering from a pathologic disorder. In this sense, the method of the invention is employed as a therapeutic method that may be applicable to any subject, including animals and plants.

In specific embodiments said therapeutic applications are employed in veterinary, wherein the subject suffering from a pathological condition is an animal. In further embodiments, said subject is a mammalian subject suffering from a pathological condition, which may include, but not limited to, inflammatory disorders, proliferative disorders, infectious diseases, immune-mediated disorders, autoimmune disorders, and neuro-degenerative and metabolic disorders.

Yet in other therapeutic applications of the present invention the subject may be a human subject suffering from a pathological condition. In this context, the term "pathological condition" refers to any abnormal anatomical or physiological condition and objective or subjective manifestations of disease or syndrome, as many pathological conditions at least indirectly related or may be affected by an immunological state of the affected subject. Of particular relevance to the present invention are human pathologies such as inflammatory disorders, proliferative disorders, infectious diseases, immune-mediated disorders, autoimmune disorders, neurodegenerative, metabolic and mental disorders.

More specifically, therapeutic applications of the present invention are intended modulation of an immunological state of said subject which results in the treatment, prophylaxis, amelioration, inhibition or delaying the onset of said pathological disorder. In this connection, the term "treatment", as used herein, means ameliorating one or more clinical indicia of disease activity in a subject having a pathologic disorder. Preventive treatment or prophylactic treatment is acting in a protective manner, to defend against or prevent something, especially a condition or disease.

Thus, it is another important aspect of the present invention to provide a method for the treatment, prophylaxis, amelioration, inhibition or delaying the onset of a pathologic disorder in a subject in need thereof. More specifically, the method of the invention may comprise: (a) providing a single or a plurality of entities. It should be noted that in certain embodiments, at least one of said entities is a biological entity. (b) subjecting the at least one of said entities to a trigger, specifically, for a selected time period under suitable conditions; and (c) exposing the subject to at least one of the triggered entities obtained in (b). In certain embodiments, such exposure modulates the physiological state of the target subject.

The terms treating, treatment and therapy as used herein refer equally to curative therapy, prophylactic or preventative therapy and ameliorating therapy. The term includes an approach for obtaining beneficial or desired physiological results, which may be established clinically and may be characterized by a skilled physician. For purposes of this invention, beneficial or desired clinical results include, but are not limited to, alleviation of symptoms, diminishment of extent of disease, stabilized (i.e., not worsening) condition, delay or slowing of progression or worsening of condition/symptoms, amelioration or palliation of the condition or symptoms, and remission (whether partial or total), whether detectable or undetectable. The term palliation, and variations thereof, as used herein, means that the extent and/or undesirable manifestations of a physiological condition or symptom are lessened and/or time course of the progression is slowed or lengthened, as compared to not administering compositions of the present invention. The term secondary prophylaxis refers to prophylactic therapy after the first occurrence of a pathological condition, e.g. inflammatory disorders, proliferative disorders, infectious diseases, immune-mediated disorders, autoimmune disorders, and neurodegenerative and metabolic disorders.

A treatment effect or therapeutic effect is manifested if there is a change in the condition being treated, as measured by the criteria constituting the definition of the terms treating and treatment. There is a change in the condition being treated if there is at least 5% improvement, preferably 10% improvement, more preferably at least 25%, even more preferably at least 50%, such as at least 75%, and most preferably at least 100% improvement. The change can be based on improvements in the severity of the treated condition in an individual, or on a difference in the frequency of improved conditions in populations of individuals with and without treatment with the method of the invention.

It is conceived that to exert its effects a method of the invention has to be carried out in an effective manner, meaning the trigger of stimulus inflicted on the non-target entity has to be delivered in an effective dose or amount, i.e. therapeutically effective amount. A therapeutically effective amount or physiologically effective amount as herein defined is the amount needed to provide an anticipated physiological response. The precise amount will depend upon numerous factors, the nature of a particular trigger as referred to above, intended use, patient considerations and others, which can be determined by one skilled in the art, based upon the information provided herein and using standard clinical procedures for determining appropriate amounts and timing of administration. It is understood that the effective amount can be the result of empirical and/or individualized (case-by-case) determination on the part of the treating health care professional and/or individual.

In some specific embodiments, at least one triggered biological entity may be at least one of an organism, an organ, a tissue, a cell, a sub-cellular entity or a cellular fraction.

In other embodiments, the at least one triggered biological entity applicable in the method of the invention may be of an autogeneic, allogenic, syngeneic or xenogeneic source to the treated subject.

In certain embodiments, the physiological state modulated by the method of the invention may be at least one of immunological state, metabolic state, physical state and chemical state.

In yet some embodiments, modulation of the physiological state of the target entity, specifically, the subject to be treated by the triggered entity is enabled by at least one waveform transmission that exists between the single or a plurality of triggered entities and the target entity (the treated subject). In more specific embodiments waveform transmission may be at least one of electromagnetic radiation, radio waves, sound waves, microwaves, infrared radiation, visible light, ultraviolet radiation, X-rays, and gamma rays.

In certain embodiments, the triggered entity used by the methods of the invention may be triggered by at least one of physical, chemical, and biological trigger or a therapeutic procedure.

In still further specific embodiments of the methods of the invention, the at least one biological entity may be exposed to an effective amount of a chemical trigger selected from natural or synthetic compounds, drugs, any preparations, extracts, mixtures or any combinations thereof.

In some specific embodiments, the physiological state modulated by the method of the invention may be an immunological state.

In further embodiments, the at least one biological entity may be exposed to an effective amount of a biological trigger selected from imuno-modulatory compounds, cytokines, hormones, growth factors, antibodies, recombinant proteins, nucleic acid sequences, amino acid sequences and any combinations thereof.

In some specific embodiments, the at least one biological entity may be exposed to a therapeutic procedure comprising surgical manipulations for example, splenectomy, or hepatectomy, to other therapeutic procedures sugar loading, starvation, sleep deprivation and depletion of immune-system components (that may be performed using antibodies). It should be further noted that triggering the triggered entity may include and involve any type of treatment that includes administering a drug of any type of a therapeutic measure, or by performing any type of procedure which can affect the biological or the non-biological entity in a beneficial or deleterious effect.

In certain embodiments, where the entity to be triggered is a biological entity, such at least one biological entity may be an immune cell of an autogeneic, allogenic, syngeneic or xenogeneic source to said subject. In some embodiments, such cell may be a lymphocytes.

In some specific embodiments, the method of the invention may further comprise an additional step of providing at least one additional mediating element placed between the subject and the at least one biological entity. It should be noted that in certain embodiments, any additional mediating element may be used, provided that the element is not an energy source and is not used for amplifying the signal or information transmitted from the triggered entity to the treated subject.

In some embodiments, the additional mediating element may include any biological or non-biological entity or substance. In more specific embodiments, such element may be a biological entity such as any cell, tissue, organ or part thereof, and body fluid. In yet some further embodiments, the additional mediating element may be a non-biological substance or entity, for example, computer, screen, any barrier, shield, container and the like. In yet some further embodiments, the at least one additional mediating element may be at least one display means or any virtual reality product or apparatus.

In specific embodiments therapeutic methods of the invention are applicable to disorders that are directly associated with dysfunction of the immune system or which can directly benefit from an improved of function of the immune system, including inflammatory disorders, proliferative disorders, infectious diseases, immune-mediated disorders, autoimmune disorders, and neurodegenerative, metabolic and mental disorders.

Inflammatory disorders, as meant herein, refer to a broad class of disorders having inflammation as a primary or secondary feature. Inflammation in this sense includes normal or adaptive immune responses of an organism to harmful stimuli, such as pathogens, damaged cells, or chemical or mechanical irritants, as well as abnormal or maladaptive responses. In other words, inflammation as meant herein refers to either acute or chronic inflammation, the first being a cascade of biochemical events ensuing in response of the body to harmful stimuli involving the local vascular system, the immune system, and various cells within the injured tissue, and the second a prolonged inflammation leading to a progressive shift in the type of cells present at the site of inflammation and is characterized by simultaneous destruction and healing of the tissue from the inflammatory process. The classical signs of acute inflammation are pain, heat, redness, swelling, and loss of function. Notable, although not limiting, examples of chronic inflammatory disorders are Ankylosing Spondylitis (AS), Antiphospholipid Antibody Syndrome (APS), Gout or Inflammatory Arthritis, Myositis, Rheumatoid Arthritis, Scleroderma, Sjogren's Syndrome, Systemic Lupus Erythematosus (SLE, Lupus), Vasculitis.

In this connection, the present methods are particularly relevant to inflammatory responses to injury and trauma and to processes of wound healing involving the skin or other tissues.

Inflammation is also an important secondary component of many diseases. An example of this is atherosclerosis, or hardening of the arteries, where inflammation can cause more damage to arteries in a failed attempt to heal the artery wall. There is also an important link between obesity and inflammation, because substances that promote inflammation are released from fat cells, as well as from other cells embedded in fat tissue.

Certain examples of immune-related or "immune-medicated" disorders include, but are not limited to, Ulcerative Colitis, Crohn's Disease, Irritable or inflammatory Bowel Disease (IBD), pediatric Crohn's disease, Alopecia Areata, Lupus, Anlcylosing Spondylitis, Meniere's Disease, Antiphospholipid Syndrome, Mixed Connective Tissue Disease, Autoimmune Addison's Disease, Multiple Sclerosis, Autoimmune Hemolytic Anemia, Myasthenia Gravis, Autoimmune Hepatitis, Pemphigus Vulgaris, Behcet's Disease, Pernicious Anemia, Bullous Pemphigoid, Polyarthritis Nodosa, Cardiomyopathy, Polychondritis, Celiac Sprue-Dermatitis, Polyglandular Syndromes, Chronic Fatigue Syndrome (CFIDS), Polymyalgia Rheumatica, Chronic Inflammatory Demyelinating, Polymyositis and Dermatomyositis, Chronic Inflammatory Polyneuropathy, Primary Agammaglobulinemia, Churg-Strauss Syndrome, Primary Biliary Cirrhosis, Cicatricial Pemphigoid, Psoriasis, CREST Syndrome, Raynaud's Phenomenon, Cold Agglutinin Disease, Reiter's Syndrome, Rheumatic Fever, Discoid Lupus, Rheumatoid Arthritis, Essential Mixed, Cryoglobulinemia Sarcoidosis, Fibromyalgia, Scleroderma, Grave's Disease, Sjogren's Syndrome, Guillain-Barre, Stiff-Man Syndrome, Hashimoto's Thyroiditis, Takayasu Arteritis, Idiopathic Pulmonary Fibrosis, Temporal Arteritis/Giant Cell Arteritis, Idiopathic Thrombocytopenia Purpura (ITP), IgA Nephropathy, Uveitis, Insulin Dependent Diabetes (Type I), Vasculitis, Lichen Planus, and Vitiligo. The compositions and delivery systems described herein can be administered to a subject to treat or prevent disorders associated with an abnormal or unwanted immune response associated with the above diseases.

Further, particular examples of an abnormal or maladaptive immune response constitute autoimmune disorders which may include, but are not limited to, Asthma, Primary sclerosing cholangitis, Alopecia Areata, Lupus, Anlcylosing Spondylitis, Meniere's Disease, Antiphospholipid Syndrome, Mixed Connective Tissue Disease, Autoimmune Addison's Disease, Multiple Sclerosis, Autoimmune Hemolytic Anemia, Myasthenia Gravis, Autoimmune Hepatitis, Pemphigus Vulgaris, Behcet's Disease, Pernicious Anemia, Bullous Pemphigoid, Polyarthritis Nodosa, Cardiomyopathy, Polychondritis, Celiac Sprue-Dermatitis, Polyglandular Syndromes, Chronic Fatigue Syndrome (CFIDS), Polymyalgia Rheumatica, Chronic Inflammatory Demyelinating, Polymyositis and Dermatomyositis, Chronic Inflammatory Polyneuropathy, Primary Agammaglobulinemia, Churg-Strauss Syndrome, Primary Biliary Cirrhosis, Cicatricial Pemphigoid, Psoriasis, CREST Syndrome, Raynaud's Phenomenon, Cold Agglutinin Disease, Reiter's Syndrome, Crohn's Disease, Rheumatic Fever, Discoid Lupus, Rheumatoid Arthritis, Essential Mixed, Cryoglobulinemia Sarcoidosis, Fibromyalgia, Scleroderma, Grave's Disease, Sjogren's Syndrome, Guillain-Barre, Stiff-Man Syndrome, Hashimoto's Thyroiditis, Takayasu Arteritis, Idiopathic Pulmonary Fibrosis, Temporal Arteritis/Giant Cell Arteritis, Idiopathic Thrombocytopenia Purpura (ITP), Ulcerative Colitis, IgA Nephropathy, Uveitis, Insulin Dependent Diabetes (Type I), Vasculitis, Lichen Planus, and Vitiligo.

Still further, methods of the invention may be particularly to treat or prevent disorders associated with an abnormal or unwanted immune response associated with cell, tissue or organ transplantation, e.g., renal, hepatic, and cardiac transplantation, e.g., graft versus host disease (GVHD), or to prevent allograft rejection.

It is conceived that methods of the invention are particularly applicable to the treatment of infectious diseases caused by pathogenic microorganisms, such as bacteria, viruses, parasites or fungi, encompassing infectious diseases transmitted in humans, as well as zoonotic diseases, i.e. infectious diseases of animals that can be transmitted to humans. In this connection, infectious disease refers to infections caused by primary pathogens that cause disease as a result of their presence or activity within the normal, healthy host, and their intrinsic virulence, as well as infections related to opportunistic pathogens can cause an infectious disease in a host with depressed resistance.

Further, immune activation of the central nervous system (CNS), in particular of microglia, is a common feature of several neurodegenerative disorders and CNS trauma. There is also emerging evidence that immune responses are also critical for neuroregeneration. It is thus conceived that the methods of the present invention may be applicable to the treatment of neurodegenerative disorders for example but not limited to Alzheimer's disease and Parkinson's disease and trauma of the CNS, inducing brain and spine injury.

In specific embodiments, methods of the invention are applicable to the treatment of Multiple Sclerosis (MS), i.e. recurrent or chronically progressive necrologic dysfunction, caused by lesions in the CNS. Pathologically, the lesions include multiple areas of demyelination affecting the brain, optic nerves, and spinal cord. The underlying etiology is uncertain, but MS is widely believed to be at least partly an autoimmune or immune-mediated disease.

Still further, it is conceived that methods of the invention are particularly applicable to the treatment of proliferative disorders. Inflammation has long been associated with the development of cancer. Epidemiological evidence points to a connection between long-term inflammation and the development of dysplasia. Epidemiologic studies estimate that nearly 15% percent of the worldwide cancer incidence is associated with microbial infection. Chronic infections, such as human papilloma virus or hepatitis B and C virus, have been associated with cervical and hepatocellular carcinoma, respectively. Immunodeficiency in AIDS is associated with Kaposi's sarcoma and inappropriate immune responses to microbes—to gastric cancer which is secondary to *Helicobacter pylori* colonization, and to colon cancer because of long-standing inflammatory bowel disease precipitated by the intestinal microflora. In many other cases, conditions associated with chronic irritation and subsequent inflammation predispose to cancer, such as the long-term exposure to cigarette smoke, asbestos, and silica.

Further, immune response and metabolic regulation are highly integrated and the proper function of each is dependent on the other. This interface can be viewed as a central homeostatic mechanism, dysfunction of which can lead to a cluster of chronic metabolic disorders, particularly obesity, type 2 diabetes and cardiovascular disease. It is thus further conceived that methods of the present invention are particularly applicable to the treatment of metabolic disorders, including all types of obesity, including endogenous obesity, exogenous obesity, hyper-insulin obesity, hyperplastic-hypertrophic obesity, hypertrophic obesity, hypothyroid obesity and morbid obesity and inflammation-mediated obesity may be treated particularly effectively in accordance with the invention.

In specific embodiments, methods of the invention are applicable to metabolic syndrome, or syndrome X, referring to a complex multi-factorial condition accompanied by an assortment of abnormalities including hypertension, hypertriglyceridemia, hyperglycemia, low high-density lipoprotein (HDL) cholesterol and abdominal obesity, which, among others, may lead to pro-thrombotic (e.g., elevated fibrinogen or plasminogen activator inhibitor-1 in the blood) and pro-inflammatory (e.g., elevated C-reactive protein (CRP) in the blood) conditions. In this connection, methods of the invention are also applicable to the disorders associated with metabolic syndrome including atherosclerosis, cardiovascular disease, stroke, and other adverse health consequences.

Still further, methods of the invention are particularly applicable for hepatitis and immune-mediated liver damage or any type of liver disease, which may be any one of viral and or bacterial and or fungal and or parasitic, alcoholic or autoimmune hepatitis, alcoholic or autoimmune cirrhosis, alcoholic fatty liver disease, non-alcoholic fatty liver disease (NAFLD), any type of liver steatosis, for example, due to other disease such as Wilson's disease or alpha 1 anti-trypsin deficiency, alcoholic or nonalcoholic steatohepatits (ASH or NASH), hepatocellular carcinoma, drug-induced liver disease and pediatric liver disease and any type of metabolic liver disease, for example, glycogen storage disease.

As indicated above pathological disorders as herein defined also encompass mental disorders. The term "mental disorders" as herein defined refers to any mental disorder defined in the Diagnostic and Statistical Manual of Mental Disorders (DSM). "Mental disorders" as used herein may also refer to mental illness, include a wide range of conditions involving genetic, metabolic, physiological, viral and environmental causes as well as injuries, traumatic condition and stress. These disorders include, but are not limited to Anxiety disorders, including panic disorder, obsessive-compulsive disorder, post-traumatic stress disorder, phobias, Bipolar disorder, Depression, Mood disorders, Personality disorders, and Psychotic disorders, including schizophrenia.

The present invention further provides a single or a plurality of entities, wherein at least one of said entities is a biological entity and wherein at least one of said entities is subjected to a trigger for use in a method for modulating a physiological state of a target biological entity.

In yet another one of its specific aspects the present invention provides a single or a plurality of entities, wherein at least one of said entities is a biological entity for use in a method for the treatment, prophylaxis, amelioration, inhibition or delaying the onset of a pathologic disorder in a subject in need thereof.

In some specific embodiments, the invention further provides a method for modulating an immunological state of a target biological entity by exposing said target entity to a single or a plurality of triggered entities. In some specific embodiments, such target biological entity may be a subject being diagnosed.

Thus, in a further aspect, the invention further provides a method for the diagnosis, prognosis and monitoring of a pathologic disorder in a subject in need, or for early diagnosis of predisposition of the subject to said disorder. In certain embodiments, the method comprising the step of: first (a), providing a single or a plurality of entities, wherein at least one of said entities is a biological entity; next (b), subjecting at least one of the at least one entity or the subject to a trigger, for a selected time period under suitable conditions; (c) detecting an end point indication in said triggered entity or triggered subject; and (d) detecting if the value obtained in said end point indication in (c) is positive or negative with respect to a predetermined standard value of a healthy population or of a population of subjects suffering from said disorder thereby diagnosing said subject. It should be noted that in certain embodiments, the end point indication may reflect the immunological state of said subject. In yet another embodiment, the end point indication may reflect the metabolic state of the subject. In still further embodiments, the end point indication may measure and therefore reflect the mental state of the subject, or alternatively, the physiological state of the subject. It should be appreciated that for evaluating the end point indication, variety of tests are available and applicable for the diagnostic method of the invention. Non limiting examples may include blood tests measuring the levels and activity of enzymes (AST, ALT), glucose, hormonal level, cytokines, lipids, blood pressure, temperature and any of the parameters indicated herein before for defining a physiological state. It should be noted that the diagnostic method of the invention implies the ability to therapeutically induce a specific state on one or more of body organs or tissues. In other embodiments, the end point indication that may be examined may include detection of specific markers of cells and levels of certain metabolites or enzymes.

A further aspect of the invention relates to a system comprising at least two entities, wherein at least one of said entities is a biological entity and wherein at least one entity is exposed to a trigger and at least one entity is not exposed to the trigger. In more specific embodiments, the non-triggered entity (an entity not exposed or subjected to a trigger) is a target entity. In more specific embodiments, the system of the invention may be applicable for modulating a physiological state of a target entity by exposure thereof to a triggered entity.

In more specific embodiments, the trigger results in modulation of the physiological states of at least one of the biological entities.

In certain embodiments, the biological entities may be at least one of an organism, an organ, a tissue, a cell, a sub-cellular component or a cellular fraction.

Still further, in certain embodiments, the biological entities of the system of the invention may be of an autogeneic, allogenic, syngeneic or xenogeneic source one to the other.

In some embodiments, the physiological state may be at least one of immunological state, metabolic state, physical state and chemical state.

In yet some other embodiments, at least one waveform transmission exists between the single or a plurality of triggered entities and the target entity of the system of the invention. More specifically, such waveform transmission may be at least one of electromagnetic radiation, radio waves, sound waves, microwaves, infrared radiation, visible light, ultraviolet radiation, X-rays and gamma rays.

Still further in some embodiments, the trigger may be at least one of physical, chemical, and biological trigger or a therapeutic procedure.

In more specific embodiments, the at least one biological entity of the system of the invention may be exposed to an effective amount of a chemical trigger selected from natural or synthetic compounds, drugs, preparations, extracts or mixtures.

In yet some further embodiments, the physiological state according to the system of the invention may be an immunological state.

In other specific embodiments, the at least one biological entity of the system of the invention may be exposed to an effective amount of a biological trigger selected from imuno-modulatory compounds, cytokines, hormones, growth factors, antibodies, recombinant proteins, nucleic acid sequences, amino acid sequences and any combinations thereof.

In yet some other embodiments, the at least one biological entity used by the system of the invention may be exposed to a therapeutic procedure comprising surgical manipulations, for example, splenectomy or hepatectomy, sugar loading, sleep deprivation, starvation and depletion of immune-system components.

In certain embodiments, the system of the invention may further comprise at least one additional mediating element placed between the entities. It should be noted that in further embodiments, such additional element is not an energy source that amplifies or extends the information transmitted between the entities of the invention.

In yet some further aspect, the invention provides a virtual reality product, device or apparatus comprising:
(a) a system comprising at least two entities, wherein at least one of said entities is a biological entity, wherein at least one entity is exposed to a trigger and wherein at least one entity is a target entity. In some specific embodiments, the target entity is not exposed to the trigger. The virtual reality product of the invention may optionally further comprise at least one of:
(b) a stimuli system which delivers at least one form of stimuli to said target entity;
(c) an input system adapted to accept any of a plurality of the target entity-generated inputs interactively generated by the target entity in response to a stimuli delivered by said stimuli system; and
(d) an output system configured to provide a presentation of one or more target entity-generated input/s.

In some specific embodiments, the stimuli system of the virtual reality product, device or apparatus of the invention may comprise at least one of a visual display system, an olfactory delivery system and an audio delivery system.

In some specific embodiments, the target entity may be a subject suffering from a pathologic disorder. Thus, the invention further provides the virtual reality product, device or apparatus according the invention for use in a method for the treatment, prophylaxis, amelioration, inhibition or delaying the onset of a pathologic disorder in said subject.

In yet a further aspect, the invention provides a method for the treatment, prophylaxis, amelioration, inhibition or delaying the onset of a pathologic disorder in a subject in need thereof. In more specific embodiments, the method comprising the step of:
(a) exposing said subject to a single or a plurality of entities, wherein at least one of said entities is a biological entity and wherein at least one of said entities is subjected to a trigger; and optionally (b) providing an interactive virtual reality environment comprising at least one of:
(i) a stimuli system which delivers at least one form of stimuli to said subject; (ii) an input system adapted to accept any of a plurality of inputs interactively generated by said subject in response to exposure to at least one triggered entity and optionally to stimuli delivered by said stimuli system; and (iii) an output system configured to provide a presentation of one or more subjects generated input/s.

Thus, in specific embodiments the current invention can be used in any product or algorithm which is based on the use of virtual reality. Virtual reality (or VR) is a technology that replicates an environment (also referred to herein as virtual reality environment), real or imagined, and simulates a user's physical presence and environment to allow for user interaction with this environment. Virtual realities artificially create sensory experiences, which can include sight, touch, hearing, and smell. Most virtual realities are displayed either on a computer monitor or with a virtual reality headset (also called head-mounted display), and some simulations include additional sensory information and focus on real sound through speakers or headphones targeted towards VR users. A "computer monitor" or a "computer display" as used herein, is an electronic visual display for computers. A monitor usually comprises the display device, circuitry, casing, and power supply. The display device in modern monitors is typically a thin film transistor liquid crystal display (TFT-LCD) or a flat panel LED display, while older monitors used a cathode ray tubes (CRT). It can be connected to the computer via VGA, DVI, HDMI, DisplayPort, Thunderbolt, LVDS (Low-voltage differential signaling) or other proprietary connectors and signals. A "virtual reality headset" provides immersive virtual reality for the wearer. VR headsets may comprise a stereoscopic head-mounted display (providing separate images for each eye), stereo sound, and head motion tracking sensors (which may include gyroscopes, accelerometers, structured light systems, etc.). Some VR headsets also have eye tracking sensors and gaming controllers. A head-mounted display (or helmet-mounted display, for aviation applications), both abbreviated HMD, is a display device, worn on the head or as part of a helmet, that has a small display optic in front of one (monocular HMD) or each eye (binocular HMD). Some advanced haptic systems now include tactile information, generally known as force feedback in medical, gaming and military applications. Furthermore, virtual reality covers remote communication environments which provide virtual presence of users with the concepts of telepresence and telexistence or a virtual artifact (VA) either through the use of standard input devices such as a keyboard and mouse, or through multimodal devices such as a wired glove or omni-directional treadmills. The immersive environment can be similar to the real world in order to create a lifelike experience for example, in simulations for pilot or combat training or it can differ significantly from reality, such as in VR games.

The simplest form of virtual reality is a 3D image that can be explored interactively at a personal computer, usually by manipulating keys or the mouse so that the content of the image moves in some direction or zooms in or out. More sophisticated efforts involve such approaches as wrap-around display screens, actual rooms augmented with wearable computers, and haptics devices that let you feel the display images.

Virtual reality can be divided into: The simulation of a real environment for training and education; and the development of an imagined environment for a game or interactive story. The Virtual Reality Modelling Language (VRML) allows the creator to specify images and the rules for their display and interaction using textual language statements.

Virtual reality is an artificial environment that is created with software and presented to the user in such a way that the user suspends belief and accepts it as a real environment. On a computer, virtual reality is primarily experienced through two of the five senses: sight and sound. The present invention suggests that virtual reality can be based on the method for information transfer described in the present invention. Any type of application of virtual reality can make use of the described system whether intentionally or non-intentionally.

In yet some other embodiments the presence of an artificial environment in virtual reality may represent a reality of information transfer which is based on the above described system.

In certain embodiments, the system of the invention can be used as part of any virtual reality based product, device, apparatus or algorithm in which transfer of information is associated with the application. These include but not limited to medicine; diagnosis of diseases; emergency conditions in medicine; therapeutics; education and training; Human simulation software; virtual reality software which enables doctors, nurses and other medical personnel to interact with others in an interactive environment; Software for training scenarios;

In certain embodiments, the system of the invention can be used as part of a virtual reality used as a diagnostic tool in that it enables doctors to arrive at a diagnosis in conjunction with other methods such as MRI scans. Virtual robotic surgery is where surgery is performed by means of a robotic device controlled by a human surgeon, which reduces time and risk of complications. It involves information transfer from the physician to the device and theoretically also in an opposite direction.

In certain embodiments, the system of the invention can be used as part of a virtual reality used in medicine, in dentistry, in nursing, in reality therapies, in phobia treatment, for treatment of post traumatic disorders and other stress conditions; for autism, for disabled.

In certain embodiments, the system of the invention can be used as part of a virtual reality used in video games, fine arts, heritage and archeology, engineering, urban and architectural design, therapies of psychological disorders or any type of disease; theme parks, films, concerts, media, charity and retail.

All scientific and technical terms used herein have meanings commonly used in the art unless otherwise specified. The definitions provided herein are to facilitate understanding of certain terms used frequently herein and are not meant to limit the scope of the present disclosure.

The term "about" as used herein indicates values that may deviate up to 1%, more specifically 5%, more specifically 10%, more specifically 15%, and in some cases up to 20% higher or lower than the value referred to, the deviation range including integer values, and, if applicable, non-integer values as well, constituting a continuous range. As used herein the term "about" refers to ±10%.

The terms "comprises", "comprising", "includes", "including", "having" and their conjugates mean "including but not limited to". This term encompasses the terms "consisting of" and "consisting essentially of". The phrase "consisting essentially of" means that the composition or method may include additional ingredients and/or steps, but only if the additional ingredients and/or steps do not materially alter the basic and novel characteristics of the claimed composition or method. Throughout this specification and the Examples and claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

It should be noted that various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible sub ranges as well as individual numerical values within that range. For example, description of a range such as from 1 to 6 should be considered to have specifically disclosed sub ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range. Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals there between.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub combination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

Disclosed and described, it is to be understood that this invention is not limited to the particular examples, methods steps, and compositions disclosed herein as such methods steps and compositions may vary somewhat. It is also to be understood that the terminology used herein is used for the purpose of describing particular embodiments only and not intended to be limiting since the scope of the present invention will be limited only by the appended claims and equivalents thereof.

It must be noted that, as used in this specification and the appended claims, the singular forms "a", "an" and "the" include plural referents unless the content clearly dictates otherwise.

The following examples are representative of techniques employed by the inventors in carrying out aspects of the present invention. It should be appreciated that while these techniques are exemplary of preferred embodiments for the practice of the invention, those of skill in the art, in light of the present disclosure, will recognize that numerous modifications can be made without departing from the spirit and intended scope of the invention.

EXAMPLES

Experimental Procedures and Methods

Animals

Male 11-12 weeks old C57BL/6 mice underwent splenectomy and/or fasting of 24 hours. Each mouse was kept in a separate cage for the duration of the experiment. Autogeneic or syngeneic splenocytes were prepared from splenectomized mice and kept for 24 hours in a tube on top of the cage at 10-20 cm distance from the mouse itself. Control cells were kept on top of cages of naïve non-splenectomized, or non-fasting mice, or on top of empty cages.

Isolation of Splenocytes and Hepatic Lymphocytes

Splenocytes and hepatic lymphocytes were isolated a. Livers and spleens were maintained in RPMI-1640 supplemented with fetal bovine serum. Spleens were crushed through a 70-μm nylon cell strainer and centrifuged (1250 rpm for 7 min) to remove debris. Red blood cells were lysed with 1 mL cold 155 mM ammonium chloride lysis buffer and immediately centrifuged (1250 rpm for 3 min). Splenocytes were washed and resuspended in 1 mL RPMI plus fetal bovine serum. The connective tissue remnants were removed. Cell viability was determined by trypan blue staining and was greater than 90%.

For intrahepatic lymphocytes, livers were first crushed through a stainless mesh (size 60, Sigma) and cell suspension was placed in a 50-mL tube for 5 min to pellet the cell debris. Lymphoprep (10 ml, Ficoll, Axis-Shield PoC AS, Oslo, Norway) was slowly added to the cell suspension in the 50-mL tubes. The tubes were then centrifuged at 1800 rpm for 18 min. Cells at the interface were collected and transferred to new tubes, which were then centrifuged at 1800 rpm for 10 min, to obtain a cell pellet depleted of hepatocytes in a final volume of 250 μl. Approximately $1 \times 10^6$ cells/mouse liver were recovered.

Flow Cytometry for Identification of Lymphocyte Subsets

Flow cytometry was performed using $1 \times 10^6$ lymphocytes in 1000 PBS. To determine the percentage of natural killer T (NKT) lymphocytes, Pacific Blue anti-mouse CD3, PE anti-mouse NK1.1 and APC-anti mouse T cell receptor (TCR) antibodies were used (eBioscience, USA). Pacific Blue anti mouse CD4, FITC-anti mouse CD8 subsets were also used (eBioscience, USA). For intracellular staining PE-anti mouse CD25 and PE-Cy7 anti mouse FOXp3 (eBioscience, USA) were used. Cells were incubated for 30 min at 4° C. in the dark, and washed and re-suspended in 200 μl PBS. Analytical cell sorting was performed on $1 \times 10^4$ cells from each group using a fluorescence-activated cell sorter (FACSTAR plus, Becton Dickinson). Only live cells were counted and unstained cells served as controls for background fluorescence. Gates were set on forward- and side-scatters to exclude dead cells and red blood cells. Data were analyzed using either the Consort 30 two-color contour plot program (Becton Dickinson, Oxnard, Calif.) or the CELL-Quest 25 program.

Measurements of Secreted Cytokines Levels

Levels of secreted cytokines were determined using standard ELISA assays.

Animal Model of Liver Damage

Concanavalin A solution (Con A; i Biomedicals, USA) consisted of 2 mg, Con A in 1 ml distilled water. Mice were intravenously (IV) injected with 250 μl Con A solution (0.5 mg/mouse).

AST and ALT Levels as Parameters of Liver Injury

Mice were tested for serum Alanine transaminase (ALT) and Aspartate aminotransferase (AST) at 24 hours after acetaminophen administration. Serum AST and ALT levels were measured by an automatic analyzer.

Example 1

Transfer of Information Between Immunological States in Exogenous Samples of Lymphocytes The studies included six groups of mice (N=4 in each group), wherein mice in groups A and B were subjected to splenectomy followed by fasting for 24 hours, groups C and D were subjected to splenectomy only, group E was subjected to fasting only and group F was not subjected to any of the above-indicated treatments. Mice groups were kept in separate cages with a tube on top of the cage containing a sample of autogeneic or syngeneic lymphocytes as detailed in Table 1 below. In groups G and H empty tubes were kept on top of empty cages. Table 1 shows groups of mice included in the studies of indirect information transfer between states.

TABLE 1

Experimental groups

| Groups | Mouse | Splenectomy | Fasting | Autogeneic cells | Syngeneic cells |
|---|---|---|---|---|---|
| A | + | + | + | + | − |
| B | + | + | + | − | + |
| C | + | + | − | + | − |
| D | + | + | − | − | + |
| E | + | − | + | − | + |
| F | + | − | − | − | + |
| G/H | − |   |   | − | − |

Lymphocytes were analyzed by FACS at times 0 and 24 hours for the presence of cell subsets expressing specific differentiation markers (CD3, CD4, CD8, CD25, FoxP3, and NK1.1) and the expression levels of secreted cytokines (IFNγ, TNFα, IL10 and TGFβ), which was repeated in three separate experiments (11A, 11B, and 11C) and in an independent lab (OL). Four mice per group were tested in OL for serum levels of IFNγ, TNFα, IL10 and TGF Mann Whitney test was performed for each experiment. Only those parameters found significant in two experiments or more, including a change in opposing directions, were used for the final analysis.

Figure 1B:
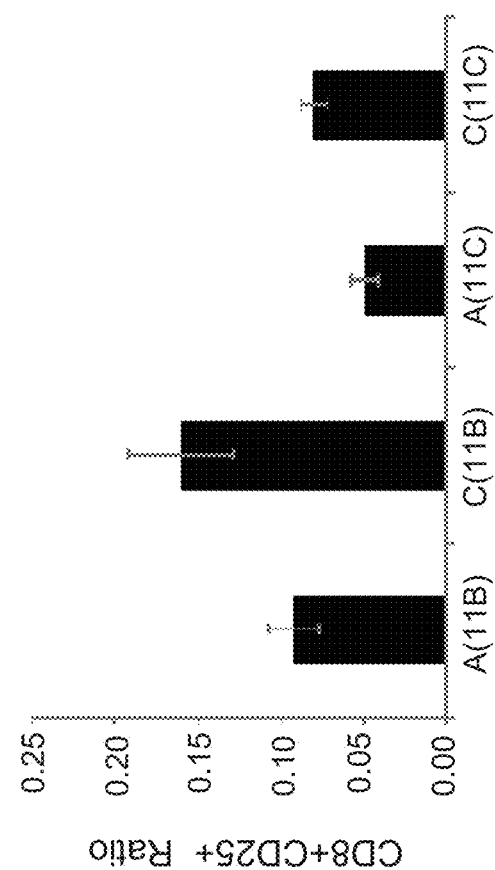

This experimental design enabled to study two types of immunological triggers: the effect of splenectomy alone or in combination with fasting and the effect of fasting, as compared to non-triggered samples, i.e. samples exposed to naïve mice or empty cages. Induction of an indirect information transfer between immunological states of immunocompromised animals and exogenous samples of lymphocytes was demonstrated in a series of experiments. FIG. 1A and FIG. 1B show the effect of animal fasting as a trigger of indirect information transfer between immunological states of exogenous samples of autogeneic or syngeneic lymphocytes. Specifically, FIG. 1A shows that autogeneic lymphocytes exposed to splenectomized and fasting animals had lower CD8+CD25+ counts (group A) compared to the non-fasting counterparts (group C) (p=0.02 and p=0.019, experiments 11B and 11C respectively). FIG. 1B further supports the effect of fasting as an immunological trigger of indirect information transfer showing increased expression levels of TNFα in syngeneic lymphocytes exposed to non-splenectomized but fasting animals (p=0.047).

The effect of splenectomy as a trigger of indirect information transfer was revealed in two independent experiments comparing immunological states of syngeneic lymphocytes samples exposed to splenectomized (group D) vs. non-splenectomized animals (groups F). FIG. 2A shows significant differences in CD8+ and ΔCD8+ cell counts (between 0 and 24 h time points) in both groups (ΔCD8+ p=0.021 and p=0.021, 11A and OL, respectively). It should be noted however that differences were manifested in both directions, suggesting that other confounding variables may affect the direction of change. Further, FIG. 2B shows that the immunological state of these syngeneic lymphocytes was clearly distinguished by the levels of at least 3 cytokines, TNFα, IFNγ and IL10, which were increased in samples exposed to splenectomized animals (p=0.014, p=0.021 and p=0.013, respectively).

Similar effects were observed for splenectomy in combination with fasting. FIG. 2C shows that the immunological state of syngeneic lymphocytes exposed to splenectomy and fasting (group B) was distinct by CD25+ and CD4+CD25+ cell counts (p=0.02, p=0.021 in 11C and p=0.03, p=0.034 in 11C, respectively). FIG. 2D shows that these samples also had significantly increased levels of TNFα, IFNγ and IL10 (p=0.021, p=0.02 and p=0.02, respectively).

These results suggest that splenectomy and fasting in combination or alone are influential triggers of indirect information transfer between immunological states of a whole organism and of an exogenous sample of syngeneic lymphocytes, which is evident by the expression of CD markers and/or secreted cytokines, expression of CD markers is further dependent on other yet unidentified conditions or factors.

The nature of this interaction between immunological states was further explored by comparing samples of autogeneic or syngeneic lymphocytes as posed to splenectomy and/or fasting and non-fasting (groups A, B, C and F) vs. samples kept on empty cages (groups G/H). FIGS. 3A to 3H show in a number of independent experiments (11A, 11B, 11C and OL) that proximity of an animal was responsible for the observed phenomenon of indirect information transfer. Specifically, FIG. 3A shows the samples of syngeneic lymphocytes exposed to splenectomized and fasting animals had distinct CD8+ counts of cells (p=0.034 and p=0.043, 11B and OL, respectively). More significant effects were observed in the levels of cytokines. FIG. 3B and FIG. 3C show that the levels of TNFα, IFNγ and IL10 were increased in autogeneic as well as syngeneic lymphocytes exposed to splenectomy and fasting (groups A and B) compared to those exposed to empty cages (p=0.021 and p=0.021 for TNFα and p=0.028, p=0.021 for IFNγ and p=0.018 for IL10, groups A and B, respectively), No such significant effects were observed in lymphocytes exposed to non-splenectomized but fasting animals (group E) (data not shown), suggesting that splenectomy is a more potent trigger of the observed changes. Significance of splenectomy and/or fasting as immunological triggers was further demonstrated in experiments comparing lymphocyte samples exposed to animals lacking these triggers vs. those exposed to empty cages (groups F and H). FIG. 3D shows that no significant changes were detected in such lymphocyte samples in 3 independent experiments using Foxp3 as an example of T-cell membrane marker.

Further, significantly elevated expression of secreted cytokines was detected in samples of autogeneic as well as syngeneic lymphocytes exposed to splenectomized non-fasting animals (groups C and D) compared to those exposed to empty group cages (H). FIGS. 3E and 3F show that autogeneic lymphocytes triggered by splenectomized animals had significantly elevated expression of TNFα, IFNγ (p=0.020 for both), but not of TNFβ. FIG. 3G shows that syngeneic lymphocytes triggered in the same way had significantly elevated expression of IFNγ, TNFα, and IL10 (p=0.021 for all). As demonstrated in FIG. 3H, low expression of TNFα was shown in lymphocytes exposed to empty cages. These results point that indirect information transfer can lead to alteration in the expression of distinct cytokines.

Example 2

Figure 4:
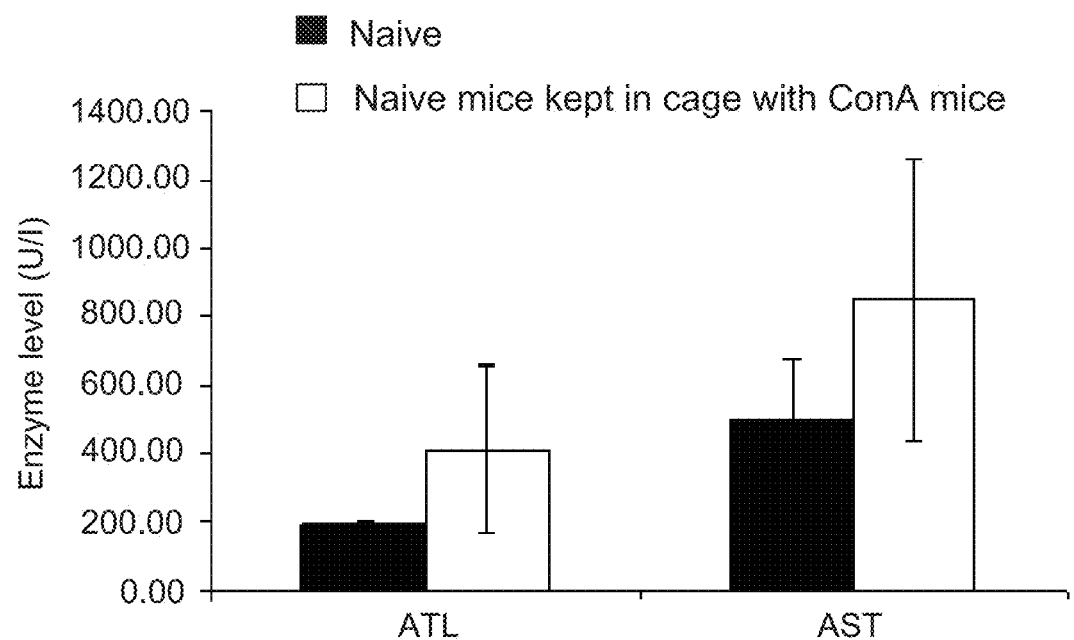
FIG. 4 shows the effect of exposure to immunologically compromised animals on disease severity in an animal model of immune-mediated liver damage in vivo measuring levels of serum ALT and AST (IU) in naïve mice (N=6) exposed (16 hours) to mice administered with Concanavalin (Con A) (N=12) vs. unexposed naïve mice serving as controls (N=2) (p<0.05).

Transfer of information affects disease severity in animal model of liver damage in vivo Studies of indirect information transfer between disease severity states on the level of a whole animal were performed using an acknowledged animal model of liver damage/hepatitis upon administering Con A and correlating disease severity to serum levels of ALT and AST. The experimental design included healthy mice (N=6) that were kept for 16 hours in the same cage with mice administered with Con A (N=12) and healthy mice kept in a separate cage serving as controls (N=2). ALT and AST serum levels were measured in all groups. FIG. 4 shows that healthy mice kept in proximity (namely in the same cage) with hepatitic mice had significantly elevated levels of serum ALT and AST compared to controls (p<0.05), suggesting the presence of certain degree of inflammation. No significant effects were observed on the severity of hepatitis in mice administered with Con A (data not shown). These results suggest the possibility of indirect information transfer between a disease state and a healthy state in distinct organisms, wherein a disease state in one serves as a trigger for the indirect information transfer of a disease state of a certain severity in the other.

Figure 5A:
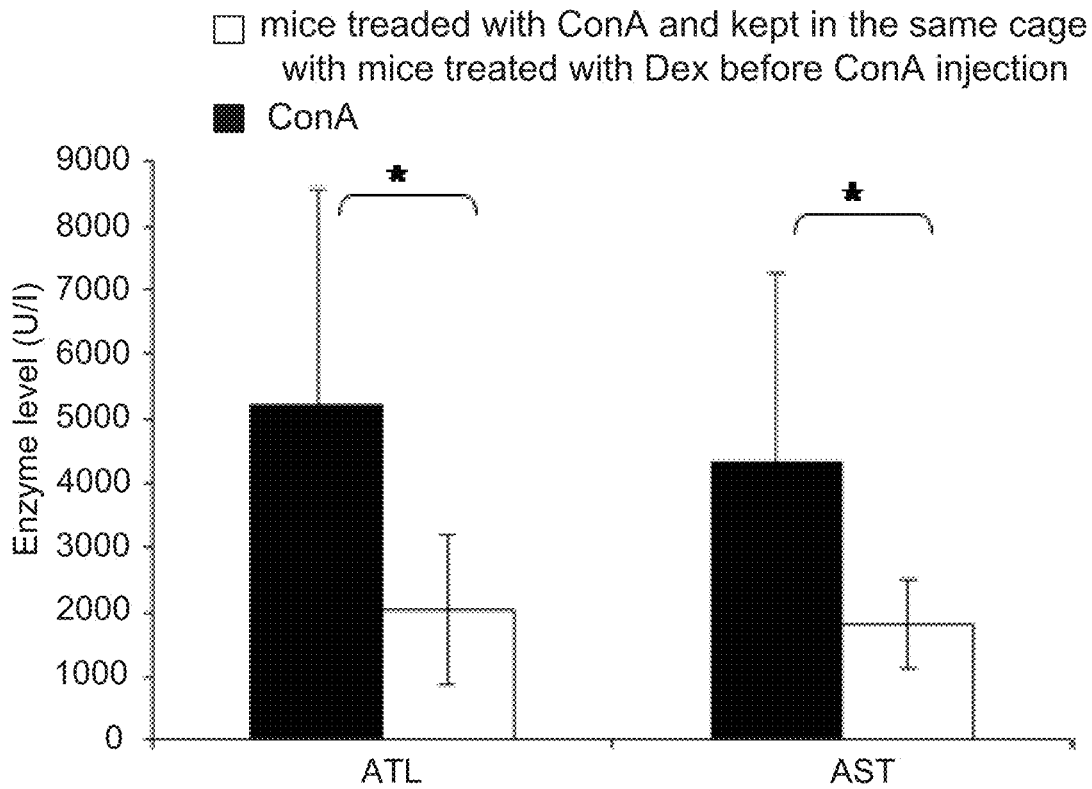
FIG. 5A to FIG. 5B show palliative effects of Dexamethasone treatment on disease severity in the model of FIG. 4, including Con A mice (N=5) exposed (16 hours) to mice treated with Dexamethasone 2 hours prior to Con A injection (N=6) (indicated by white bars) vs. non-exposed Con A mice (N=6) (indicated by black bars) (p<0.05).
Figure 5B:
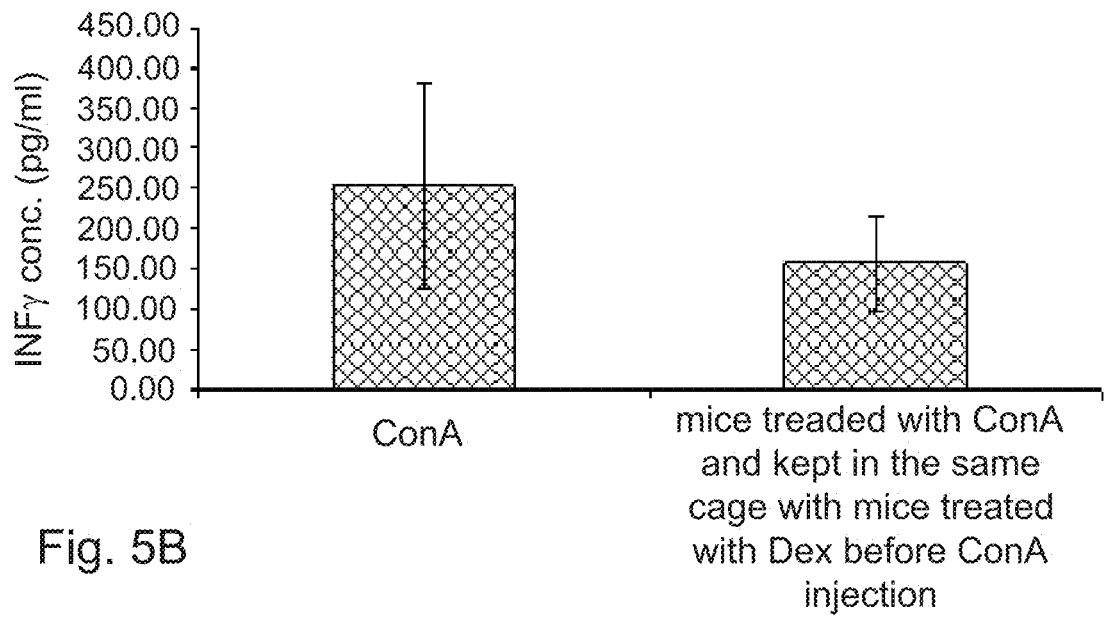

Induced Immuno-Modulation as a Trigger for Information Transfer that Affects Disease Severity In Vivo Assuming the possibility of indirect information transfer between disease severity states between one or more organisms, it would be therefore conceivable that treating of a disease severity in one would affect the disease severity in the other, especially since the existence of an indirect information transfer phenomenon has been shown on the immunological level in Example 1. This possibility was explored in the same animal model using Dexamethasone as a reparative immunomodulator of Con A induced liver damage. These experiments included mice administered with Con A (N=5) that were kept for 16 hours in the same cage with mice treated with Dexamethasone two hours prior to ConA injection, control groups were healthy naïve mice (N=2), or mice injected with Con A (N=5) or mice treated with Dexamethasone (N=6), all groups kept in separate cages. Serum levels of, ALT, AST and IFNγ, as acknowledged markers of liver damage, were measured 16 hours after ConA injection. FIGS. 5A and 5B show that ALT, AST and IFNγ levels were significantly lower in ConA mice kept together with mice receiving Dexamethasone prior to ConA injection (p<0.01).

Example 3

Immunomodulation of Exogenous Samples of Cells and Tissues to Induce Information Transfer Basing on the above findings of information transfer between disease severity states and possibility of their immumomodulation on the level of a whole animal, it could be conceived that this indirect information transfer could be reproduced and potentially controlled between a whole organism positioned in a sufficient proximity to an exogenous sample of lymphocytes or other cells, tissues or organs. Thus a series of experiments were carried out in the above model of liver damage, where Con A mice kept in separate cages were exposed to samples of splenocytes harvested from Con A mice treated or untreated with Dexamethasone. FIG. 6 shows promising palliative anti-inflammatory effects in Con A mice exposed to splenocytes treated with Dexamethasone as measured by ALT and AST serum levels ($p<0.05$). FIG. 7 further supports these findings in showing that Con A mice kept in proximity to spleens (group 2) and livers (group 3) harvested from naïve mice did not show such palliative effects, specifically when compared to the effect shown when exposed to splenocytes harvested from Con A mice treated with Dexamethasone (group 1).

These surprising findings suggest that a disease state of an affected organism could be modulated by exposure of said organism to an exogenous sample of syngeneic cells previously treated for the same disease. In other words, triggering of an exogenous sample may be used to induce an indirect information transfer between disease states in vivo or an information transfer that can affect diseased states. Still further, according to these and previous findings (Example 1) this indirect transfer of information between immunological states could be controlled by the direction of the immunological trigger, i.e. may be triggered either in an organism or in exogenous sample of cells.

This phenomenon was further explored in an experiment, in which Con A mice were exposed to exogenous splenocytes or liver cells (N=5) harvested from naïve or Dexamethasone treated donors. Table 2 summarizes the test groups and treatments.

TABLE 2

Experimental groups

| Group | Mice | Con A | Dexamethazone | Cell samples |
|---|---|---|---|---|
| A | N = 5 | + | − | — |
| B | N = 5 | + | + | — |
| C | N = 5 | + | − | Splenocytes naïve donors |
| D | N = 5 | + | − | Splenocytes from Dexamethasone treated donors |
| E | N = 5 | + | − | Liver cells from healthy donors |
| F | N = 5 | + | − | Liver cells from Con A mice |

Figure 8:
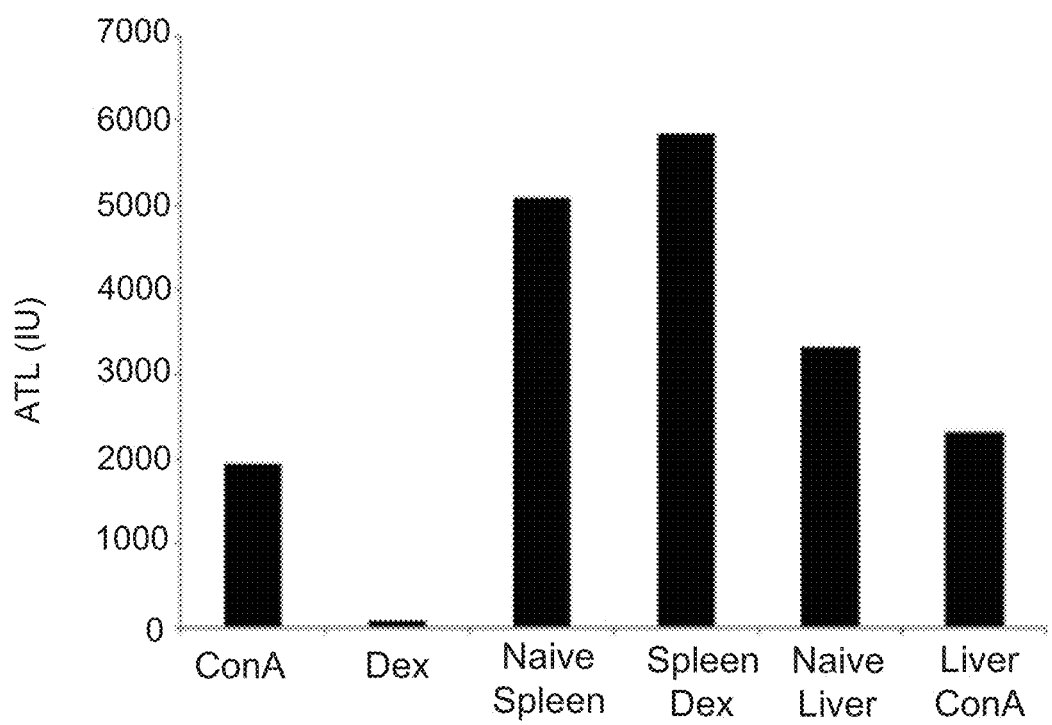
FIG. 8 shows the effect exposure to samples of cells harvested from liver or spleen from naïve or Dexamethasone treated donors on disease severity in vivo referring to groups in Table 2, comparing serum ALT levels (IU) in untreated Con A mice (Con A, group A), Con A mice treated with Dexamethasone (Dex, group B), Con A mice exposed to liver or spleen cells from healthy donors (naïve liver or spleen, groups E and C, respectively), and those exposed to spleen cells from Dexamethasone treated donors (spleen Dex, group D) and to liver cells from other affected Con A mice (liver Con A, group F).

FIG. 8 shows serum ALT levels as an indices of an inflammatory state in various groups. Mice treated with Dexamethasone (group B) had significantly improved ALT levels compared to other groups of mice. Although all other groups of mice were characterized with higher ALT levels, a closer look at these data suggested that these groups have marked inter-individual variability, especially groups D and E. Relying on the physical basis of the indirect information transfer phenomenon suggest that these data should be interpreted on individual basis.

Example 4

Effect of Sleep Deprivation on Long Distance Expression of Immune Epitopes in Humans The study design of the clinical trial is detailed in Table 3 below. In brief, human subjects in groups A (regular sleep overnight) and B (sleep deprivation overnight) were bled on day 1 of the experiment between 8 and 9 AM (namely before undergoing regular sleep or sleep deprivation). Blood tubes were tested for T cell markers using FACS, where tubes A1 and B1 were tested on the day of experiment; tubes A2 and B2 were kept in the lab and tested 24 hours later; tubes A3 and B3 were kept in a pocket of the same subject and tested 24 hours later; and tubes A4 and B4 were kept in a pocket of another subject subjected to the same condition (sleep deprivation or regular sleep) and tested 24 hours later. Subjects were tested again following 24 hours. Each subject was tested twice following a regular 6-8 hours of sleep, and following an on call duty in which he slept less than 3 hours.

TABLE 3

Clinical trial design

| Groups | | Sleep Deprivation Study Scheme version 3 |
|---|---|---|
| A: after overnight sleep | 8 AM Draw blood | Tube A1: Tested by FACS (serum sample is frozen for cytokines) Tube A2: Kept in the lab Tube A3: Kept in a pocket or next to subject's bed at night Tube A4: Kept on another subject from the same group |
| B2: after sleep deprivation overnight | 8 AM Draw blood | Tube B1: Tested by FACS (serum sample is frozen for cytokines) Tube B2: Kept in the lab Tube B3: Kept in a pocket or next to subject's bed at night Tube B4: Kept on another subject from the same group |

The effects of sleep deprivation on body lymphocyte samples are shown in Table 4 in which distribution of various lymphocyte markers (CD4, CD8 and CD25) in samples A3 (regular sleep) and B3 (sleep deprivation) in three subjects were compared. Table 4 shows values as rates of change in marker distribution.

TABLE 4

Comparison between tubes A3 to B3 in three patients

| | CD4 | CD25 | CD4 + CD25 | CD8 | CD25 | CD8 + CD25 | CD4/CD8 |
|---|---|---|---|---|---|---|---|
| Subject 1 | | | | | | | |
| A3 | 72.56 | 0.1 | 0.5 | 10.98 | 0.7 | 0.04 | 6.6 |
|  | 73.06 | 0.6 |  | 11.02 | 0.74 |  | 6.6 |
| B3 | 97.19 | 0.01 | 0.22 | 1.58 | 0.13 | 0.01 | 61.5 |
|  | 97.41 | 0.23 |  | 1.59 | 0.14 |  | 61.3 |
| Subject 2 | | | | | | | |
| A3 | 53.17 | 0.31 | 0.61 | 36.52 | 0.8 | 0.25 | 1.5 |
|  | 53.78 | 0.92 |  | 36.77 | 1.05 |  | 1.5 |
| B3 | 95.46 | 0 | 0.08 | 7.18 | 0 | 0 | 13.3 |
|  | 95.54 | 0.08 |  | 7.18 | 0 |  | 13.3 |
| Subject 3 | | | | | | | |
| A3 | 16.43 | 0.71 | 1.43 | 15.24 | 0.71 | 0.48 | 1.1 |
|  | 17.86 | 2.14 |  | 15.72 | 1.19 |  | 1.1 |
| B3 | 42.78 | 0 | 0.06 | 27.42 | 0.42 | 0.07 | 1.6 |
|  | 42.84 | 0.06 |  | 27.49 | 0.49 |  | 1.6 |

Table 4 shows significant differences in the markers distributions in groups A (blood samples in a proximity of a subject under regular sleep) and B (blood samples in a proximity of a subject under sleep deprivation). These differences were particularly evident in a decrease in CD4+ CD25+ and in CD8+CD25+ cells, and in increase in the CD4/CD8 lymphocyte ratio. These data point to long distance effects between a whole organism, such as the human organism and out of body sample of lymphocytes, sleep deprivation serve a trigger for modulation of an immunological status of said sample. From a broader perspective, these findings imply the existence of an out of body transfer of information.

Example 5

Reproducing Induction of an Immunological State in Exogenous Samples of Lymphocytes Table 5 shows design of an experiment reproducing induction of an immunological state in exogenous samples of lymphocytes, essentially reproducing EXAMPLE 1. In brief, the splenocytes from each mouse in groups 1M (A) and 3M (C) were divided to 4 tubes, wherein group 1M (A) cells were divided to tubes A1-4, B5-8, E17-20 and G1-4; group 3M (C) cells were divided to tubes C9-12, D13-16, F21-24 and G5-8. Each cell tube contained the same number of cells ($15\text{-}20\times10^6$) in 1 ml culture medium. Groups 1M (A), 2M (B) and 5M (E) were fasted for 21-24 hours (no food). Groups 3M (C), 4M (D) and 6M (F)—No fasting. Cell tubes were put on the still grid in the mouse cage and subjected to the procedures as detailed in Table 5 below.

TABLE 5

Study design

| Group | N | Animal ID | Splenectomy | Cells in cage (cells source) |
|---|---|---|---|---|
| 1M (A) | 4 | 1-4 | + | Self (A1-4) |
| 2M (B) | 4 | 5-8 | + | Non-self (A1-4) |
| 3M (C) | 4 | 9-12 | + | Self (C9-12) |
| 4M (D) | 4 | 13-15, 25 | + | Non-self (C9-12) |
| 5M (E) | 4 | 17-20 | − | Non-self (A1-4) |
| 6M (F) | 4 | 21-24 | − | Non-self (C9-12) |
| 7M (G) | | No mice | NA | Non-self (A1-4) |
| | | | | Non-self (C9-12) |

| Study Day | Procedures |
|---|---|
| Acclimation | Group allocation |
| 1 | Splenectomy 1M-4M |
| | Splenocytes preparation from groups 1M & 3M |
| | FACS on splenocytes from groups 1M & 3M |
| | Splenocytes introduction to animal cages (with or without fasting) |

TABLE 5-continued

Study design

| | |
|---|---|
| 2 | Termination |
| | FACS on splenocytes from A-G tubes |
| | ELISA on splenocytes sup from A-G tubes |

Similarly to EXAMPLE 1, borderline differences were found in the distribution of CD8, CD25 markers in lymphocyte samples exposed to splenectomy and/or fasting, in combination or alone, compared to control samples. Further, borderline differences were found in the levels of the IL10 cytokine in lymphocyte samples exposed to splenectomy and/or fasting compared to controls.

I claim:

1. A method for treating a liver disease or disorder in a mammalian subject in need thereof, the method comprising
taking a biological sample comprising at least $1\times10^6$ lymphocytes cells, the sample comprising syngeneic cells relative to the mammalian subject, from at least one other mammalian subject who received treatment for the liver disease or disorder, wherein prior to the taking of the biological sample, the at least one other mammalian subject underwent a triggering event involving at least one of (i) fasting, (ii) a splenectomy and (iii) when the other mammalian subject is human, sleep deprivation; and
exposing the mammalian subject having the liver disease or disorder exogenously to the biological sample by positioning the biological sample within a predetermined distance from the mammalian subject continuously for a multitude of hours without physical contact with the mammalian subject's body.

2. The method according to claim 1, wherein, the predetermined distance does not exceed 10 meters.

3. The method according to claim 1, wherein said mammalian subject in need thereof and said at least one other mammalian subject are human subjects.

4. The method according to claim 3, wherein the biological sample comprises blood.

5. The method according to claim 1, wherein said liver disease or disorder is damaged liver or hepatitis.

6. The method of claim 1, wherein the multitude of hours is at least 24 hours.

\* \* \* \* \*